United States Patent
Hinds, Jr. et al.

(10) Patent No.: US 10,457,947 B2
(45) Date of Patent: Oct. 29, 2019

(54) TARGETING OF HUMAN GLUCOCORTICOID RECEPTOR BETA IN CANCER

(71) Applicant: The University of Toledo, Toledo, OH (US)

(72) Inventors: Terry D. Hinds, Jr., Toledo, OH (US); Lucien McBeth, Toledo, OH (US)

(73) Assignee: The University of Toldeo, Toledo, OH (US)

( * ) Notice: Subject to any disclaimer, the term of this patent is extended or adjusted under 35 U.S.C. 154(b) by 0 days.

(21) Appl. No.: 16/082,188

(22) PCT Filed: Mar. 7, 2017

(86) PCT No.: PCT/US2017/021064
§ 371 (c)(1),
(2) Date: Sep. 4, 2018

(87) PCT Pub. No.: WO2017/155929
PCT Pub. Date: Sep. 14, 2017

(65) Prior Publication Data
US 2019/0085337 A1 Mar. 21, 2019

Related U.S. Application Data

(60) Provisional application No. 62/306,209, filed on Mar. 10, 2016.

(51) Int. Cl.
*C12N 15/113* (2010.01)
*A61K 38/00* (2006.01)
*A61K 47/64* (2017.01)
*A61P 35/00* (2006.01)
*A61K 38/16* (2006.01)

(52) U.S. Cl.
CPC ........ *C12N 15/1138* (2013.01); *A61K 38/162* (2013.01); *A61K 47/6455* (2017.08); *A61P 35/00* (2018.01); *C12N 2310/3181* (2013.01); *C12N 2310/3513* (2013.01)

(58) Field of Classification Search
None
See application file for complete search history.

(56) References Cited

U.S. PATENT DOCUMENTS

2014/0004565 A1* 1/2014 Rossomando ..... C12N 15/1135
435/70.3

FOREIGN PATENT DOCUMENTS

WO  WO-2012140234 A1 * 10/2012 ........... C12N 15/113

* cited by examiner

*Primary Examiner* — Tracy Vivlemore
(74) *Attorney, Agent, or Firm* — MacMillan, Sobanski & Todd, LLC

(57) ABSTRACT

A peptide nucleic acid (PNA) referred to herein as Sweet-P, compositions comprising the methods of making the same, mid methods of using the same, are described.

24 Claims, 25 Drawing Sheets
(11 of 25 Drawing Sheet(s) Filed in Color)
Specification includes a Sequence Listing.

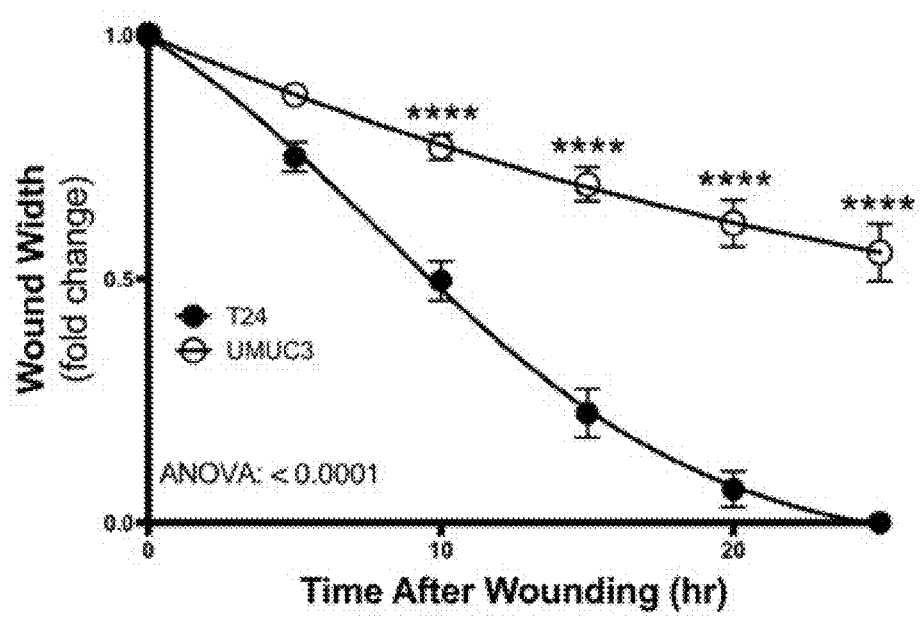
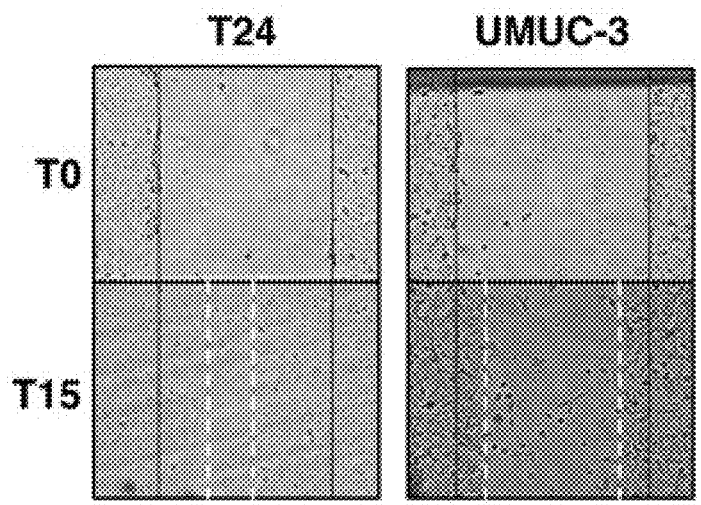
FIG. 1C

3'UTR of human GRβ (with TGA stop codon)

TGAttttcatcccagcaatcttggcgctcaaaaaatagaactcaatgagaaaaagaagattatgtgcactt
cgttgtcaataataagtcaactgatgctcatcgacaactataggaggctttcattaaatgggaaaagaag
ctgtgcccttttaggatacgtgggggaaaagaaagtcatcttaatatgtttaattgtggatttaagtgct
atatggtggtgctgttgaaagcagatttatttcctatgtatgtgttatctggccatcccaacccaaactg
ttgaagtttgtagtaacttcagtgagagttggttactcacaacaaatcctgaaaagtatttttagtgtttg
taggtattctgtgggatactatacaagcagaactgaggcacttaggacataacactttttggggtatatata
tccaaatgcctaaaactatgggaggaaaccttggccacccccaaaaggaaaactaacatgatttgtgtctat
gaagtgctggataattagcatgggatgagctctggcatgccatgaaggaaagccacgctccttcagaat
tcagaggcaggagcaattccagtttcacctaagtctcataatttttagttccctttttaaaaaccctgaaaa
ctacatcaccatggaatgaaaaatattgttatacaatacattgatctgtcaaacttccagaaccatggtag
ccttcagtgagatttccatcttggctggtcactccctgactgtagctgac■■■■■■■ttttgtgtgt
gtgtgtctggttttagtgtcagaaggaaataaaagtgtaaggaggacacttaaacccctttgggtggagt
ttcgtaatttcccagactatttcagcaacctggtccacccaggattagtgaccaggttttcaggaaagg
atttgcttctctctagaaaatgtctgaaaggattttattttctgatgaaaggctgtatgaaaatacctcc
tcaaataacttgctaactacatatagattcaagtgtgtcaatattctatttgtatattaaatgctatat
aatgggacaaatctatatt■■■■■■gtat■■■■■■ttaagaagctttttcattattttttcatcacagt
aatttttaaaatgtgtaaaaattaaaaccagtgactcctgtttaaaataaaagtttgtagtttttttattcat
gctgaataatatctgtagttaaaaaaaagtgtcttttttacctacgcagtgaaatgtcagactgtaaac
cttgtgtggaaatgttcaacttttattttttcatttaaatttgctgttctggtattaccaaaccacacatt
tgtaccgaattggcagtaaaatgttagccatttacagcaatgccaaatatggagaaaatcataataaaaaa
atctgcttttcatta ■■■■
target sequence:  GGCATTA
mutant sequence:  AAAAAAA ■■■■
target sequence:  ATACTGT
mutant sequence:  AAAAAAA ■■■■
sequence:  gtgaatgtg
mutate to:  AAAAAAAAA

FIG. 7

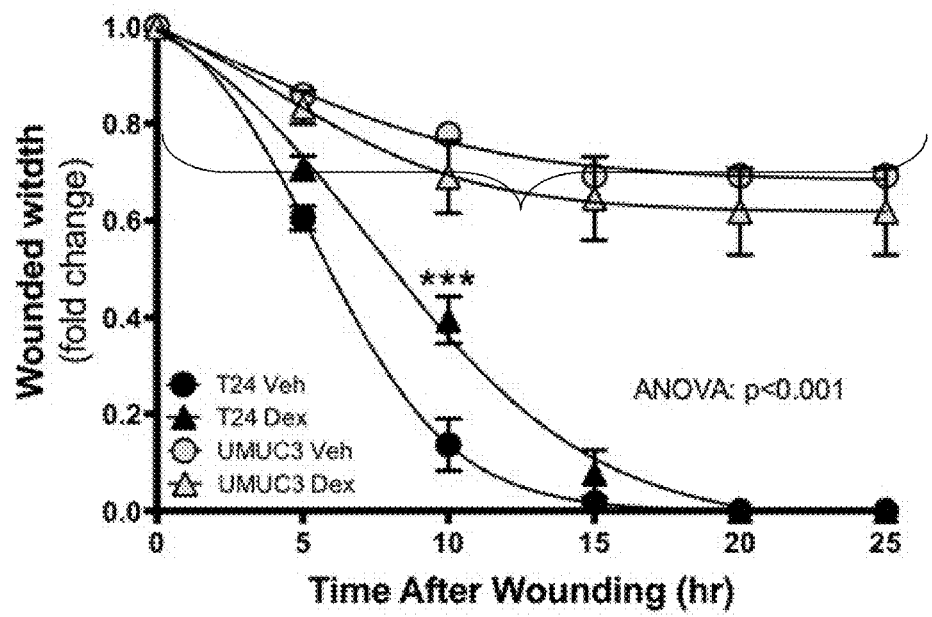
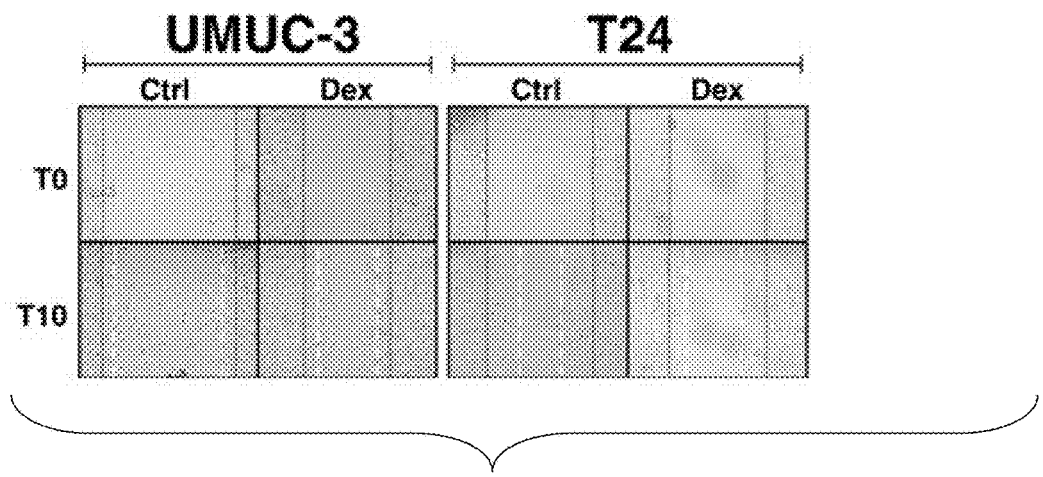
FIG. 8A

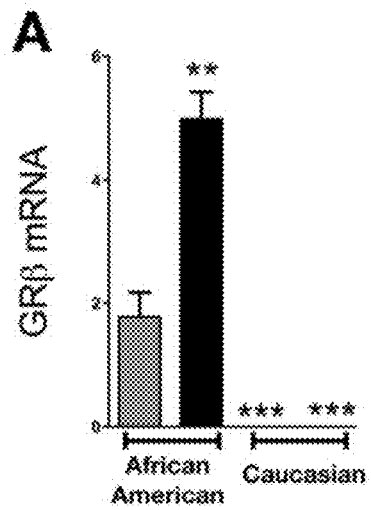
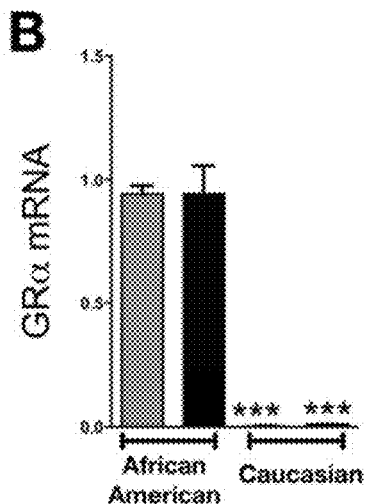
FIG. 14A
FIG. 14B
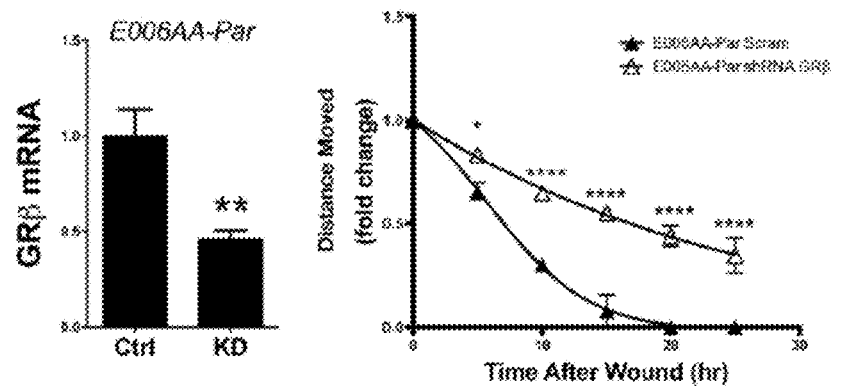
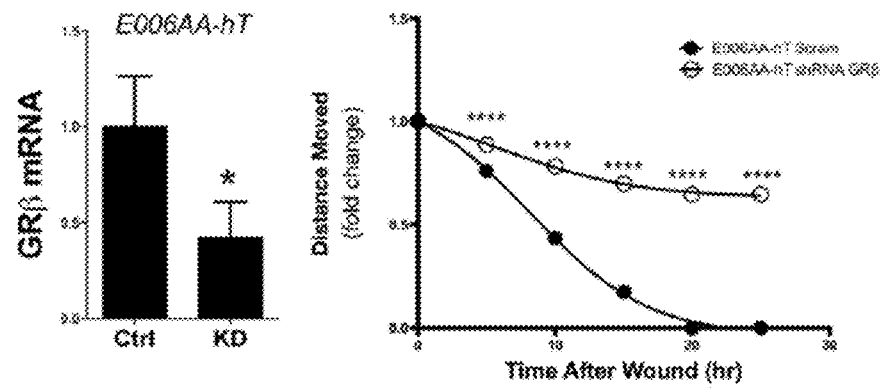
FIG. 15

TARGETING OF HUMAN GLUCOCORTICOID RECEPTOR BETA IN CANCER

RELATED APPLICATIONS

This application claims priority to United States Provisional Application Ser. No. 62/306,209 filed under 35 U.S.C. § 111(b) on Mar. 10, 2016, the disclosure of which is incorporated herein by reference in its entirety.

STATEMENT REGARDING FEDERALLY SPONSORED RESEARCH

This invention was made with no government support. The government has no rights in this invention.

SEQUENCE LISTING

The instant application contains a Sequence Listing which has been submitted electronically in ASCII format and is hereby incorporated by reference in its entirety. Said ASCII copy, created on Mar. 6, 2017, is named 430_57720_SEQ_LIST_ID2016-49.txt and is 3,894 bytes in size.

BACKGROUND OF THE INVENTION

Bladder cancer is observed worldwide having been associated with a host of environmental and lifestyle risk factors. Bladder cancer was the fourth most prevalent cancer in men, and fifth overall in 2015. Glucocorticoids (GCs) have been used in bladder cancer for their protective properties against the toxic effects of chemotherapy. GCs may cause resistance to cisplatin, which is a treatment commonly used for bladder cancer. The GC receptor (GR) is expressed as different isoforms, GRα and GRβ, which are a result of alternative splicing of a single gene. GCs bind and activate the ligand-binding GR isoform GRα, which is a transcription factor that increases genes involved in cell cycle arrest and apoptosis. GRβ lacks the ligand-binding domain for GCs, and has been shown to be inhibitory to GRα. A higher total GR expression has been correlated with a better prognosis in bladder cancer. However, the specific roles of GRα or GRβ in bladder cancer are unknown.

Work in the art has yielded a conundrum, in that GCs can suppress bladder cancer invasion but also induce proliferation. GCs are used to inhibit growth in hematological cancers and solid tumors. However, long-term GC treatment can increase the risk of bladder cancer, for uncertain reasons. It has been shown that GRβ can suppress the phosphatase and tensin homolog deleted on chromosome 10 (PTEN) expression and increase Akt1 guided proliferation. Furthermore, GRβ has been shown to be involved in the migratory process of astrocytes and the development of glioblastoma. It has also been shown that the effectiveness of GCs in patients is reduced with a lower GRα/GRβ ratio. Factors that regulate the expression of GRα or GRβ may influence the response to GCs. GC resistance in sepsis has been shown to be affected by microRNA 124 (miR124), which down-regulates GRα, causing increased immune cell growth.

Naturally occurring mutation in the AUUA motif of the 3' untranslated region (UTR) of GRα and GRβ results in increased mRNA stability and protein expression. Targeting of the 3' UTR of genes by miRNAs may alter mRNA stability, which is believed to be involved in processes that regulate cancer development or progression. Some miRNAs have been proposed as biomarkers to detect and predict the severity of bladder cancer. The miRNAs that may regulate bladder cancer proliferation may be of importance, which has been shown by miR125b targeting of the E2F3 transcription factor, a tumor suppressor that regulates the cell cycle. Furthermore, miR145 and miR133a decrease bladder cancer aggressiveness by targeting fascin actin-bundling protein 1 (FSCN1), which binds β-catenin to increase motility and invasion. Higher-grade bladder tumors have been shown to express elevated miR144, which has also been shown to promote cell proliferation in nasopharyngeal carcinoma. However, the involvement of miRNAs, and their regulation of GRα or GRβ, in bladder cancer development or progression is unknown.

There is a need in the art for a better understanding of bladder cancer. Moreover, it would be advantageous to develop new therapeutic agents and methods for the treatment, amelioration, or prevention of bladder cancer.

SUMMARY OF THE INVENTION

Provided is a composition comprising a peptide nucleic acid (PNA) consisting of the sequence TGCCATACACAGTAT [SEQ ID NO:1]. In certain embodiments, the PNA is attached to a solubility enhancing molecule. In certain embodiments, the solubility enhancing molecule comprises an O-linker. In certain embodiments, the PNA is conjugated to a cell-penetrating peptide. In particular embodiments, the cell-penetrating peptide comprises a modified tat protein. In particular embodiments, the modified tat protein consists of the amino acid sequence VQRKRQKLMP [SEQ ID NO:2]. In certain embodiments, the PNA is attached to an O-linker and to a modified tat protein consisting of the amino acid sequence VQRKRQKLMP [SEQ ID NO:2].

Also provided is a peptide nucleic acid (PNA) consisting the sequence TGCCATACACAGTAT [SEQ ID NO:1].

Also provided is a pharmaceutical composition comprising an effective amount of a composition described herein, and a pharmaceutically acceptable carrier, diluent, or adjuvant.

Also provided is a method of modulating GRβ expression in cells, the method comprising administering to cells an effective amount of an agent capable of blocking miR144 binding to GRβ, and modulating GRβ expression in the cells. In certain embodiments, the cells are cancer cells. In certain embodiments, the cells are in a human subject. In certain embodiments, the agent comprises a PNA consisting of the sequence TGCCATACACAGTAT [SEQ ID NO:1].

Also provided is a method of treating a GRβ-related disease, the method comprising administering an effective amount of an agent to a subject in need thereof, wherein the effective amount of the agent blocks miR144 binding to GRβ in the subject, and treating a GRβ-related disease in the subject. In certain embodiments, the agent blocks miR144 binding in the 3'UTR of GRβ. In certain embodiments, the agent comprises a peptide nucleic acid (PNA). In particular embodiments, the PNA consists of the sequence TGCCATACACAGTAT [SEQ ID NO:1]. In particular embodiments, the PNA is conjugated to a modified TAT protein. In certain embodiments, the GRβ-related disease is selected from the group consisting of: bladder cancer, prostate cancer, lung cancer, leukemia, lupus, and asthma.

Also provided is a method of hindering migration of a GRβ-related cancer, the method comprising administering an effective amount of a composition described herein to a subject in need thereof and hindering migration of a GRβ-related cancer. In certain embodiments, the GRβ-related cancer is selected from the group consisting of bladder cancer, prostate cancer, lung cancer, and leukemia. In certain embodiments, the subject is a human subject.

Also provided is a method for regulating GRβ expression in cells, the method comprising administering an effective amount of a composition described herein to cells and regulating expression of GRβ in the cells. In certain embodiments, GRβ is suppressed in the cells. In certain embodiments, the cells are cancer cells. In particular embodiments, the cancer is selected from the group consisting of bladder cancer, prostate cancer, lung cancer, and leukemia. In certain embodiments, the cells are in a human subject.

Also provided is a method of determining coverage of health insurance reimbursement or payments, the method comprising denying coverage or reimbursement for a treatment, wherein the treatment comprises a composition described herein.

Also provided is a kit for preparing a pharmaceutical composition, the kit comprising a first container housing a peptide nucleic acid (PNA) consisting of the sequence TGCCATACACAGTAT [SEQ ID NO:1]; and a second container housing an O-linker or a modified tat protein consisting of the amino acid sequence VQRKRQKLMP [SEQ ID NO:2].

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIGS. 1A-1C: GRβ and GRα expression and migration in UMUC3 and T24 human bladder cancer cells. GRβ and GRα expression was measured by immunofluorescence. (FIG. 1A.) Secondary antibodies (labeling GRα or GRβ) are shown in green, DAPI (nuclei labeling) are shown in blue, and bright field images are shown in gray (scale bar=25 μm). GRβ and GRα mRNA expression were measured by Real-Time PCR. (FIG. 1B). *, $p<0.05$; , $p<0.01$ (versus UMUC3) (±S.E.; n=3). Migration was measured in UMUC3 and T24 cells at 5, 10, 15, 20, and 25 hours post wounding as the fold-changed wound width remaining. (FIG. 1C). The images are of the migration assay at 0 and 15 hours post wounding, with wound edges marked at T0 (black solid line) and T15 (white dashed line). ANOVA $p<0.0001$; Bonferoni comparisons **, $p<0.0001$ (versus UMUC3) (±S.E.; n=6).

FIG. 2A shows a schematic of the human GR gene to show the shRNA target site for GRβ. Knockdown of GRβ was confirmed by Real-Time PCR. (FIG. 2B.) , $p<0.01$ (versus T24 Scramble) (±S.E.; n=3). Migration was measured in the T24 Scramble and T24 GRβ shRNA cells at 5, 10, 15, 20, and 25 hours post wounding. (FIG. 2C.) Images of the migration assay at 0 and 25 hours post wounding are shown, with wound edges marked at T0 (black solid line) and T15 (white dashed line). ANOVA $p<0.001$; Bonferoni comparisons , $p<0.01$; ***, $p<0.001$. (versus T24 Scramble) (±S.E.; n=6).

FIG. 7: The 3'UTR of human GRβ [SEQ ID NO: 5] with the mutation of the binding sites for miRNAs. The sequence is shown, with the miR181a, b, c, & d binding site highlighted in green, the miR144 binding site highlighted in blue, and the miR33a binding site highlighted in red.

FIGS. 8A-8B: The effect of dexamethasone treatment on cell migration and miRNA expression in UMUC-3 and T24 bladder cancer cells. Migration was measured in the UMUC-3 and T24 cells that were treated with either vehicle or 100 nM dexamethasone for 30 minutes prior to wounding, and is presented as the fold-change in the wound width remaining (FIG. 8A). Images of the migration assay at 0 and 10 hours post wounding are shown, with wound edges marked at T0 (black solid line) and T15 (white dashed line). ANOVA $p<0.001$; Bonferoni comparisons ***, $p<0.0001$ (versus Vehicle) (±S.E.; n=6). Total RNA was extracted from the UMUC3 and T24 cells after treating with either vehicle, 100 nM dexamethasone, or 100 nM Insulin in dialyzed media for 2 hours before harvesting, and miRNA expression was measured by Real-Time PCR (FIG. 8B). *, $p<0.05$; (Dex versus Veh); $, $p<0.05$; (Ins versus Veh); ##, $p<0.01$; ##, $p<0.001$; (T24 versus UMUC3) (±S.E.; n=6).

FIG. 9D shows immunostaining of human GRβ and GRα with 10 nM Sweet-P treatment for 48 hours in T24 bladder cancer cells. FIG. 9E shows Sweet-P treatment for 48 hours and then 2 hours of dexamethasone in T24 cells and Real-time PCR analysis of FKBP51 and tumor necrosis factor α (TNFα). *, p<0.05; **, p<0.01 (versus no dex or Sweet-P control) (±S.E.; n=3). FIG. 9F shows immunostaining of mTOR and PTEN with 10 nM Sweet-P treatment for 48 hours in T24 bladder cancer cells. Migration was measured in the T24 after being treated with 10 nM Sweet-P for 48 hours prior to wounding, and is presented as the fold-change for the wound width remaining (FIG. 9G). Images of the migration assay at 0 and 10 hours post wounding are shown, with wound edges marked at T0 (black solid line) and T15 (white dashed line). ANOVA p<0.001; Dunnet comparisons *, p<0.05; , p<0.01; *, p<0.0001 (versus 0 nM) (±S.E.; n=6).

FIG. 13A: Structural domains of the human AR and the polymorphic trinucleotide CAG repeats in exon 1 that encode for a polyglutamine chain [SEQ ID NO: 6] located upstream of the activation factor-1 (AF-1) domain. AF=activation factor, DBD=DNA-binding domain, H=hinge region, LBD=ligand-binding domain, HSP90=HSP90 binding region. FIG. 13B: The polyglutamine (QQQQ) chain [SEQ ID NO: 4] in the AR gene of Caucasian men [SEQ ID NO: 7] is longer than African American [SEQ ID NO: 8] and causes a reduced AR gene response. Z=zinc finger, DHT=dihydrotestosterone.

FIGS. 14A-14B: Real-time PCR of GRβ and GRα in African American and Caucasian prostate cancer cells.

FIG. 15: Lentiviral shRNA suppression of human GRβ in E006AA-Par and E006AA-hT African American prostate cancer cells suppresses migration. *, P<0.05 and **, P<0.01; (scramble vs GRβ KD). N=12.

DETAILED DESCRIPTION OF THE INVENTION

Figure 1A:
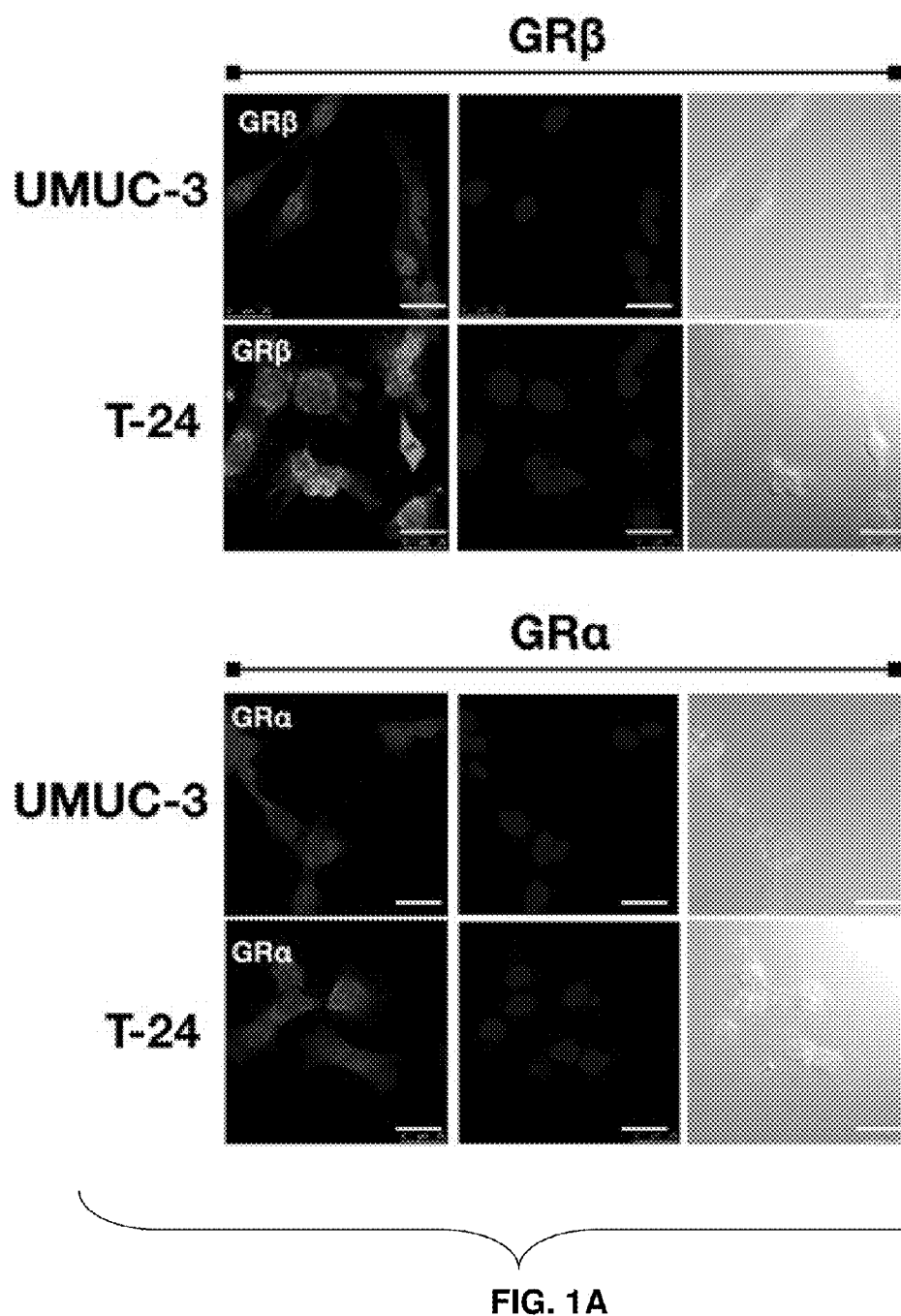

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

The present disclosure relates to compositions and methods for the treatment of GRβ-related diseases. Certain compositions and methods described utilize a peptide nucleic acid (PNA). A PNA is a non-naturally occurring, artificially synthesized polymer similar to DNA or RNA. Despite the name, PNAs are not actually acids or peptides. Rather, a PNA is a polyamide (pseudopeptide) which can hybridize to nucleic acids (RNA or DNA) with sequence specificity. Because PNA is a polyamide, it has a C-terminus (carboxyl terminus) and an N-terminus (amino terminus). The N-terminus of the sequence of a PNA can be thought of as equivalent to the 5-hydroxyl terminus of an equivalent DNA or RNA oligonucleotide. However, structurally, PNAs differ from nucleic acids. Although both can employ common nucleobases (A, C, G, T, and U), the backbones of these molecules are distinct. Whereas DNA and RNA have a deoxyribose and ribose sugar backbone, respectively, a PNA's backbone is composed of repeating N-(2-amino-ethyl)-glycine units linked by peptide bonds. The various purine and pyrimidine bases of a PNA sequence are linked to the backbone by a methylene bridge ($—CH_2—$) and a carbonyl group ($—(C=O)—$) (i.e., a methylene carbonyl moiety). In other words, PNAs are synthetic polyamides composed of repeating units of 2-aminoethylglycine to which the bases A, C, G, T, and U are attached through a methylene carbonyl group. PNAs are neutral in charge and can be water soluble. Because a PNA's backbone contains no charged phosphate groups, the binding between PNA/DNA strands tends to be stronger than DNA/DNA strands due to the lack of electrostatic repulsion. PNAs can hybridize to nucleic acids in both a parallel and antiparallel orientation.

Provided herein is a PNA, referred to as Sweet-P, having the sequence TGCCATACACAGTAT [SEQ ID NO:1]. Sweet-P can be synthesized through any method suitable for PNA synthesis. PNAs are generally synthesized by adaptation of standard peptide synthesis procedures. Methods for the chemical assembly of PNAs are known. See, for example, U.S. Pat. Nos. 5,539,082, 5,527,675, 5,623,049, 5,714,331, 5,736,336, and 5,773,571, each of which is incorporated herein by reference. Chemicals and instrumentation for the support-bound automated chemical assembly of PNAs are commercially available. Chemical assembly of a PNA is analogous to solid phase peptide synthesis, wherein at each cycle of assembly the oligomer possesses a reactive alkyl amino terminus which is condensed with the next synthon to be added to the growing polymer.

Purine-rich PNAs, as well as longer-length PNAs, tend to be less soluble. Therefore, in some embodiments, Sweet-P is attached to a solubility enhancing molecule, such as an O-linker, to make the peptide soluble. Either or both termini of Sweet-P can be modified with an O-linker, lysine, or other solubility enhancing molecules.

In some embodiments, Sweet-P is conjugated to a delivery vehicle, such as a cell-penetrating peptide (CPP), to allow the peptide to enter cells. Suitable CPPs include modified trans-activator of transcription ("tat") proteins. A non-limiting example of a suitable modified tat protein consists of the amino acid sequence VQRKRQKLMP [SEQ ID NO:2]. However, the skilled practitioner will recognize that a wide variety of suitable delivery vehicles other than this particular modified tat protein, and other than CPPs in general, can be utilized to deliver Sweet-P into target cells.

There is a pathway in anti-inflammatory glucocorticoid signaling that impacts certain cancers and diseases. Sweet-P suppresses glucocorticoid receptor beta (GRβ) and thereby inhibits expression and migration of GRβ-involved cancers and diseases. As described in the Examples below, Sweet-P is capable of blocking the binding site of miR144 in the 3'UTR of human GRβ, which causes inhibited expression and, as a result, decreased migration of bladder cancer cells. Sweet-P also causes decreased expression of GRβ in prostate cancer cells and lung cancer cells. Sweet-P is therefore useful for treating, or hindering the migration of, bladder cancer, prostate cancer, and lung cancer. Moreover, because Sweet-P inhibits GRβ, Sweet-P is useful in treating any GRβ-related cancer or disease, such as, but not limited to, bladder cancer, prostate cancer, lung cancer, leukemia, lupus, and asthma. Sweet-P is also useful for modulating GRβ expression in cells, which Sweet-P accomplishes by blocking the miR144 binding site in the 3'UTR of GRβ.

Pharmaceutical compositions of the present disclosure comprise an effective amount of Sweet-P with or without solubility-enhancing molecules and/or delivery vehicles (an "active" compound), and/or additional agents, dissolved or dispersed in a pharmaceutically acceptable carrier. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid, or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543, 158, 5,641,515, and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In particular embodiments, the compositions described herein are useful for treating, preventing, or ameliorating GRβ-related diseases, including GRβ-involved cancers. Furthermore, the compositions herein can be used in combination therapies. That is, the compositions can be administered concurrently with, prior to, or subsequent to one or more other desired therapeutic or medical procedures or drugs. As a non-limiting example, the compositions can be administered in a combination therapy with one or more anti-cancer agents. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

It is further envisioned that the compounds and methods described herein can be embodied in the form of a kit or kits. A non-limiting example of such a kit is a kit for preparing a pharmaceutical composition, the kit comprising Sweet-P and a delivery vehicle or O-linker in separate containers, where the containers may or may not be present in a combined configuration. Many other kits are possible, such as kits further comprising a pharmaceutically acceptable carrier, diluent, or excipient. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Further provided is a method of determining coverage of health insurance reimbursement or payments, the method comprising denying coverage or reimbursement for a treatment, wherein the treatment comprises Sweet-P.

EXAMPLES

Example 1

In these Examples, it is shown that GRβ enhances migration of human bladder cancer cells. Three potential miRNA target sites in the 3' UTR of human GRβ were found, and miR144 positively affected human GRβ expression. Additionally, blocking the binding site of miR144 in the 3' UTR of human GRβ inhibited expression, and, as a result, decreased migration, of bladder cancer cells. An inverse effect on the glucocorticoid receptor (GR) isoform signaling that is believed to lead to bladder cancer is shown. Similar GRα expression levels in the transitional uroepithelial cancer cell lines T24 and UMUC-3 were found. However, the T24 cells showed a significant ($p<0.05$) increased expression of GRβ compared to UMUC-3, which also correlated with higher migration rates. Knockdown of GRβ in the T24 cells resulted in a decreased migration rate. Mutational analysis of the 3' untranslated region (UTR) of human GRβ revealed that miR-144 may positively regulate expression. Indeed, overexpression of miR144 increased GRβ by 3.8 fold. In addition, miR-144 and GRβ were upregulated during migration. A peptide nucleic acid (Sweet-P) conjugated to a cell penetrating-peptide was used to block the binding site for miR144 in the 3'UTR of GRβ. Sweet-P effectively prevented miR144 actions and decreased GRβ expression, as well as the migration of the T24 human bladder cancer cells. Therefore, GRβ has a significant role in bladder cancer, and serves as a therapeutic target for the disease. Moreover, Sweet-P serves as a therapeutic agent for the treatment of bladder cancer and other GRβ-related cancers and diseases.

Materials & Methods

Cell Lines and Culture

The human uroepithelial carcinoma cell lines UMUC-3 and T24 (ATCC) were routinely cultured and maintained in Minimum Essential Medium (MEM) containing 10% fetal bovine serum (FBS) with 1% antibiotic-antimycotic. Cells were maintained at 37° C. and 5% $CO_2$. Media was changed to MEM containing 10% Dialyzed-FBS with 1% antibiotic antimycotic 24 hours before hormone treatments.

RNA Extraction for mRNA Quantification and Real-Time PCR Analysis

Total RNA was extracted from cell cultures using the 5-Prime PerfectPure® RNA Cell Kit (Fisher Scientific Company, LLC). Total RNA was read on a NanoDrop 2000® spectrophotometer (ThermoFisher Scientific, Wilmington, Del.) and cDNA was synthesized using High Capacity cDNA Reverse Transcription Kit (Applied Biosystems). PCR amplification of the cDNA was performed by quantitative real-time PCR using TrueAmp SYBR Green qPCR SuperMix® (Smart Bioscience). The thermocycling protocol consisted of 10 min at 95° C., 40 cycles of 15 sec at 95° C., 30 sec at 60° C., and 20 sec at 72° C., and finished with a melting curve ranging from 60-95° C. to allow distinction of specific products. Normalization was performed in separate reactions with primers to GAPDH.

RNA Extraction for miRNA Quantification and Real-Time PCR Analysis

Total RNA was extracted from cell cultures using the miRNeasy® Mini Kit (Qiagen). Total RNA was read on a NanoDrop 2000® spectrophotometer (Thermo Fisher Scientific, Wilmington, Del.) and cDNA was synthesized using the miScript RT Kit (Qiagen). PCR amplification of the cDNA was performed by quantitative real-time PCR using miScript SYBR® Green PCR Kit (Qiagen). The thermocycling protocol consisted of 15 min at 95° C., 40 cycles of 15 sec at 94° C., 30 sec at 55° C., and 30 sec at 70° C., and finished with a melting curve ranging from 60-95° C. to allow distinction of specific products. The miScript Primer Assay® primers were purchased from Qiagen. Normalization was performed in separate reactions with primers to Hs_RNU6-2_11, At_U19_1, and Hs_SNORD61_11.

Immunofluorescence and Microscopy

Cells were seeded onto a glass coverslip placed in a 6-well plate and grown were grown to desired confluence. Cells were then fixed with 3% paraformaldehyde, permeated with PBS containing 0.25% Triton X (PBST), and blocked with PBST containing 1% BSA. Slides were then stained with either anti-hGRα Rabbit IgG or anti-hGRβ Rabbit IgG antibodies obtained from Antibody Research. Secondary staining was performed using anti-Rb IgG 488 antibody from Life Technologies. Coverslips were planted onto slides with Fluoromount-G®, and DAPI was added to stain nuclei. Slides were magnified using a Leica Microscope with a 63X oil Immersion lens. Images were acquired in the XYZ plane in 1 μm steps with a 63X oil objective (NA 1.40). Images were acquired with the LAS AF® software in sequential scan mode. AlexaFluor488® was excited at 488 nm with collection at 500-558 nm and DAPI was excited with the multi-photon (MP) laser tuned to 790 nm with collection at 420-500 nm. Images are 2D projections of the of image stack as labeled. Three images were taken per slide and ImageJ software was used to measure the immunofluorescence of each cell (average 40 cells) in the images.

Migration Assay

Cells were seeded on a 6-well plate and grown for 24 hours until a monolayer of 90% confluent cells was obtained. A scratch wound in the cell monolayer was introduced using a sterile pipette tip. Images were taken at the time of wounding, and every 5 hours thereafter. Migration was measured as the fold change of the width of the wound remaining. To determine miRNA and mRNA expression during the scratch (wounding assay), total RNA was collected using the miRNeasy® Mini Kit (Qiagen) (described above) at 0 and 3 hours after the migration.

Generation of Lentiviral Constructs

To establish a T24 cell line that has hGRβ stably knocked down, the pGFP-C-shLenti plasmid containing either GRβ shRNA (CCAGAAAGCACATCTCACACATTAATCTG) [SEQ ID NO: 3] or scrambled shRNA (Origene) was packaged into a lentiviral construct using the Lenti-vpak® Packaging Kit (Origene) by transfection in 293-GP2 cells. The supernatants were harvested and the cell debris was removed by filtration through 0.45 µM filter. The supernatant was used to infect T24 cells after addition of polybrene (10 ug/ml, Sigma Chemical Co., St. Louis, Mo.) to establish cell lines with stable expression of hGRβ shRNA (T24 GRβ KD) or expressing scrambled shRNA (T24 Scramble). After 72 h the cells were initially selected using Puromycin® (10 µg/mL). Cells were then secondarily selected by sorting through flow cytometry for GFP.

Transient Transfection

For transient transfection, cells were plated on a 6-well or 12-well dish in MEM containing 10% FBS. Cells were washed with OPTI-MEM and transfected using GeneFect® (Alkali Scientific, Inc.), according to the manufacturer's 157 protocol. OPTI-MEM was removed after 12 h and MEM containing 10% FBS was added.

Promoter Reporter Assays

The expression vector pMirTarget containing the 3'UTR of hGRβ (hGRβ 3'UTR-luc) was purchased from Origene. The binding sites were mutated using the QuikChange Lightning Multi Site-Directed Mutagenesis Kits® (Agilent Technologies). Successful mutations were confirmed through sequencing by Operon MWG. Cells were seeded onto a 12-well plate and grown overnight. Transient transfection was performed as described above. To determine the effect of Sweet-P on the T24 bladder cancer cells, the cells were treated 24 h after transfection for 48 hours post transfection, 3'UTR GRβ-Luc WT or mutant expression was measured by luciferase, and pRL-CMV Renilla reporter for normalization to transfection efficiency, using the Promega dual luciferase assay system (Promega, Madison, Wis.).

miRNA Overexpression

The cloning vector pCMV-MIR containing the miR144 sequence was purchased from Origene. Cells were seeded on a 6-well plate, and transient transfection of the plasmid was completed as described above. After 48 hours-post transfection, RNA was harvested.

Targeting of the Human GRβ mRNA

A peptide nucleic acid (PNA) (Sweet-P) conjugated to a cell penetrating peptide (CPP) targeting the miR144 binding site in the 3'UTR of the human GRβ was designed using the PANAGENE® website (www.panagene.com). The Sweet-P targeting sequence was: (TGCCATACACAGTAT) [SEQ ID NO:1]. The Sweet-P sequence targeted the miR144 binding site in the 3' UTR of human GRβ. (FIG. 7.) All PNAs were attached to an O-linker and a modified tat protein (VQRKRQKLMP) [SEQ ID NO:2] for delivery into the cell. Treatment with Sweet-P was performed for 48 hrs before the cells were analyzed.

Statistical Analysis

Data were analyzed with Prism 5® (GraphPad® Software, San Diego, Calif.) using analysis of variance combined with Tukey's post-test to compare pairs of group means or unpaired t tests. Additionally, two-way ANOVA was utilized in multiple comparisons, and followed by either the Bonferroni or Dunnet post hoc analyses to identify interactions. p values of 0.05 or smaller were considered statistically significant.

Results

GRβ & GRα in Human Bladder Cancer Cells

Figure 1B:
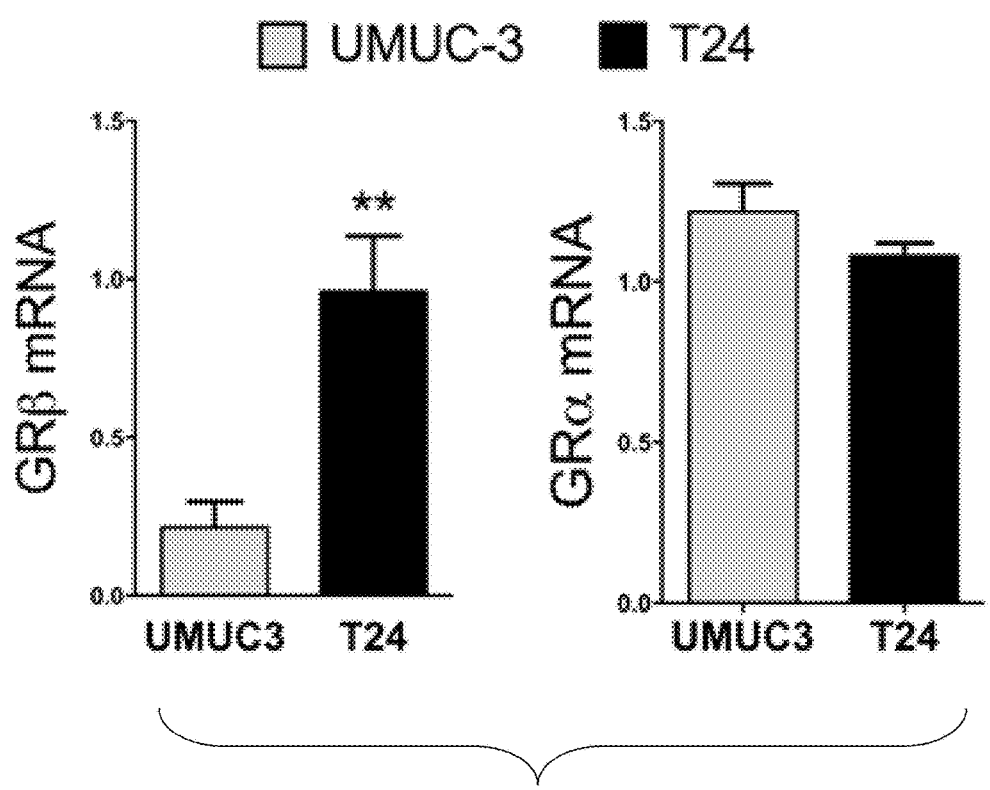
Figure 2A:
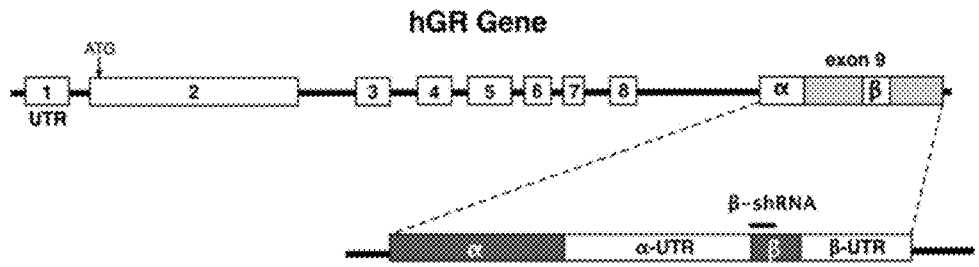
FIGS. 2A-2C: Knockdown of GRβ reduces migration of human bladder cancer cells.
Figure 2B:
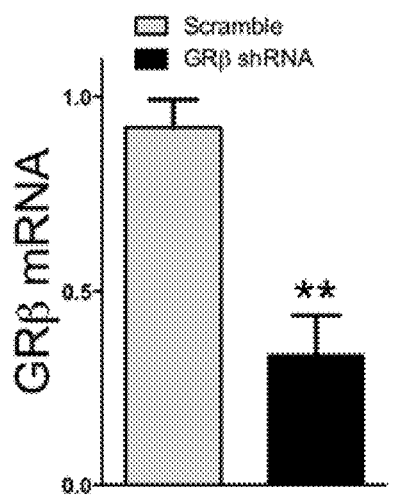
Figure 2C:
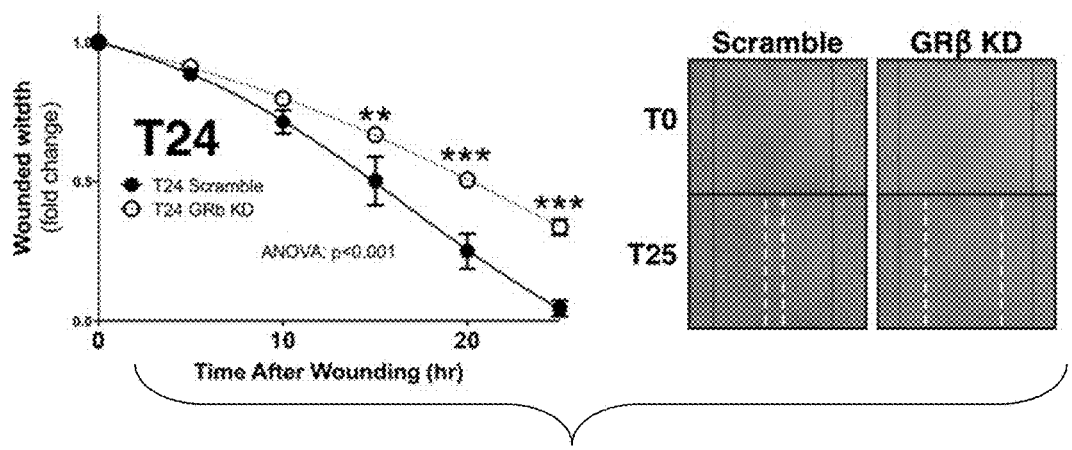

GRβ is involved in regulating cellular pathways that are known to be involved in cancer. However, previous analyses have been performed in non-cancerous mouse fibroblast and 3T3-L1 cells. To examine the two GR isoforms in human bladder cancer, their expression in two transitional uroepothelial cancer cell lines, UMUC3, and T24, was examined. As shown by immunofluorescence staining and mRNA expression, the T24 cell line was found to have a higher expression of GRβ compared to the UMUC-3 (FIGS. 1A & 1B). GRα had similar levels by immunofluorescence and mRNA in the T24 cells. To determine if human bladder cancer cells that have higher GRβ expression are more migratory, a wound healing migration assay was conducted. The T24 cells with higher GRβ expression had a significantly (ANOVA $p<0.0001$) faster migration compared to the UMUC-3 (FIGS. 1C & 1D). To show the effect of GRβ in the T24 cell line, a stable cell line with an shRNA lentivirus targeting human GRβ (FIG. 2A) was established. The knockdown of GRβ expression in the T24 cells (64% reduction) (FIG. 2B) resulted in a significant (ANOVA: $p<0.001$) decrease in migration (FIG. 2C).

Figure 3A:
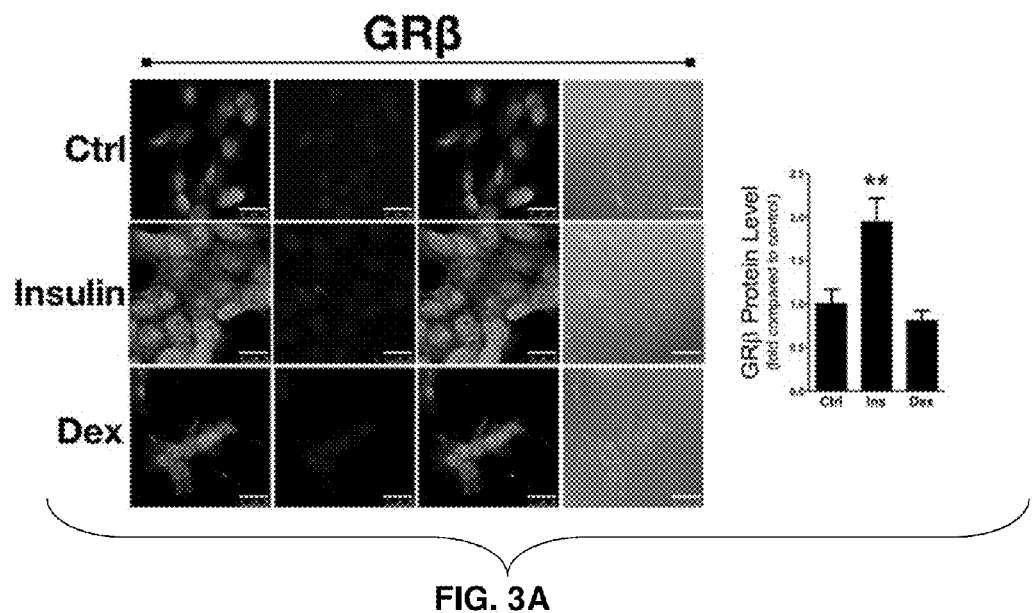
FIGS. 3A-3D: Dexamethasone and insulin treatment in T24 cells (FIGS. 3A-3B) and UMUC-3 cells (FIGS. 3C-3D). GRβ and GRα expression and location were measured using immunofluorescence with control (vehicle treatment), dexamethasone, or insulin treatments. Cells were seeded onto coverslips in media containing 10% dialyzed FBS for 24 hours before treating. Cells were treated with 100 nM insulin, 100 nM dexamethasone, or vehicle for 30 minutes. Secondary antibodies (labeling of human GRα or GRβ) are shown in green, DAPI (nuclei labeling) are shown in blue, a merge of the green and blue images are shown in panel 3 to represent localization, and a bright field image is shown in gray (scale bar=25 μm). Data are represented as fold change compared to control. , $p<0.01$; *, $p<0.001$; ****, $p<0.0001$ (versus control) (±S.E.; n=3).
Figure 3B:
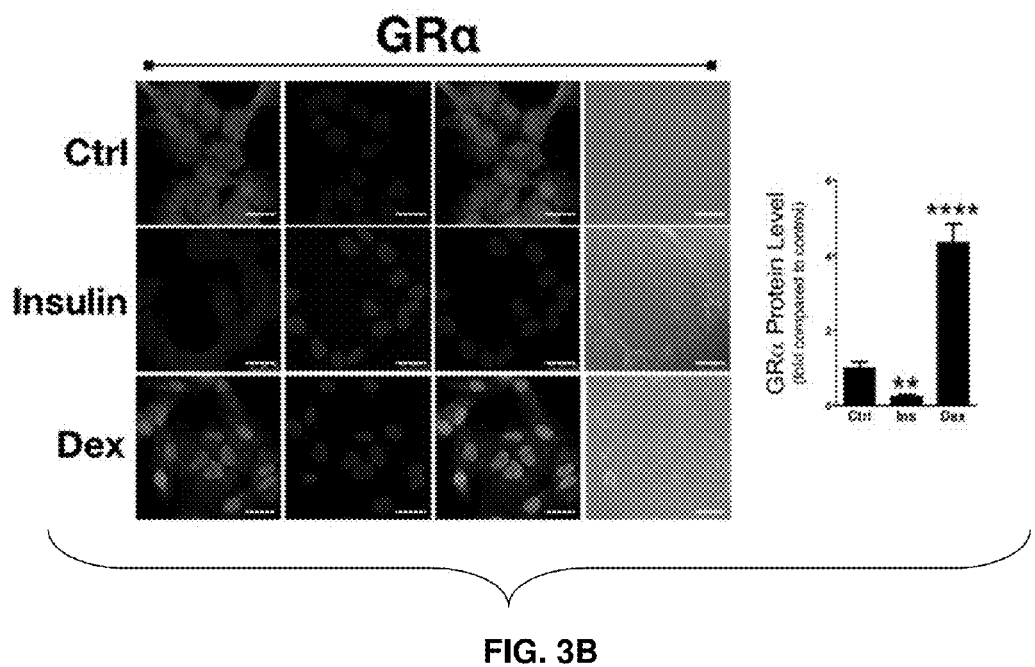
Figure 3C:
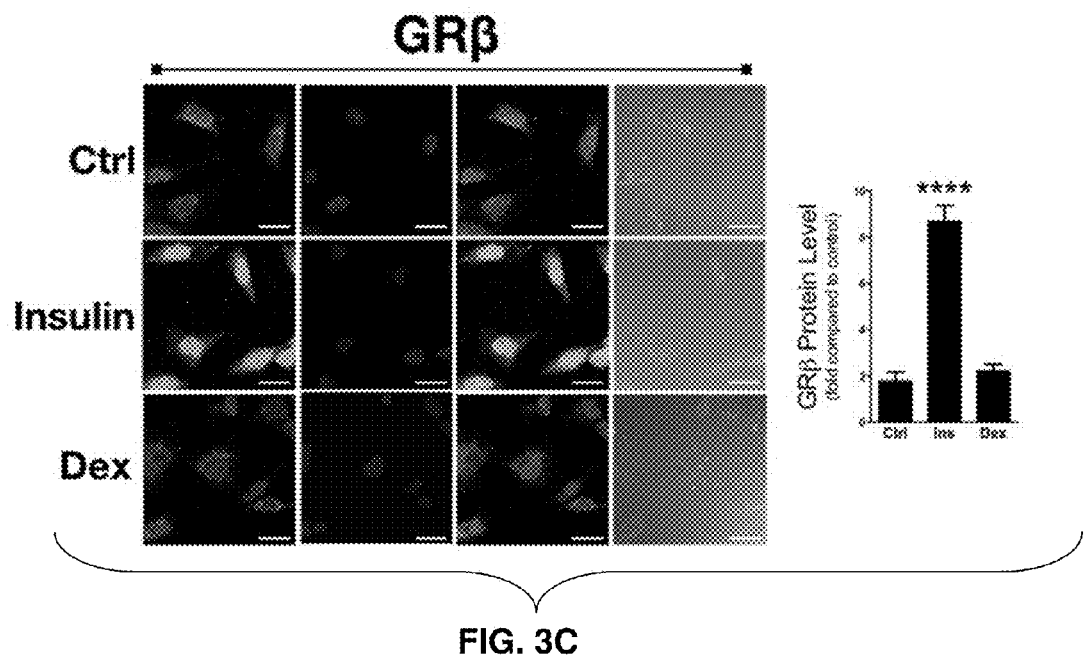
Figure 3D:
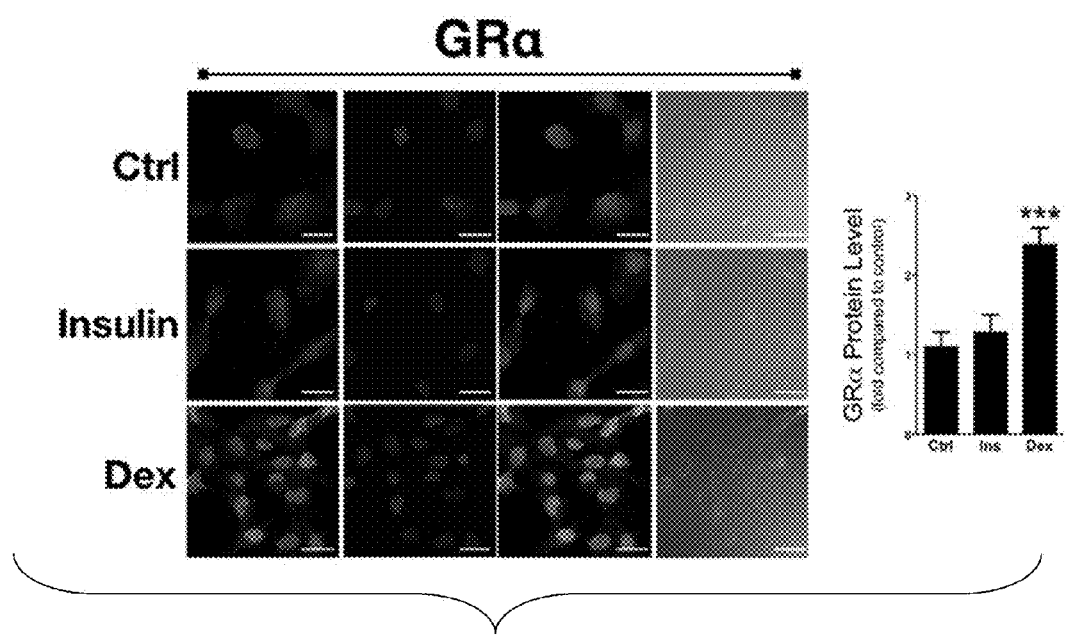

The Effect of Insulin and Dexamethasone on GRβ & GRα in Human Bladder Cancer Cells Insulin increases GRβ mRNA and protein expression in the cells and livers of mice. To determine the effect of insulin or dexamethasone (Dex) on GR isoform localization and expression, the T24 and UMUC-3 bladder cancer cells were treated for 30 minutes and labeled with human GRα or GRβ antibodies for immunofluorescence staining Insulin treatment significantly increased GRβ expression in the T24 ($p<0.01$) and UMUC-3 ($p<0.0001$) cells (FIGS. 3A & 3C). However, there was no difference observed in GRβ expression or localization in the human bladder cancer cells with Dex treatment, even though it has previously been shown that GCs increase GRβ in normal mouse cells. As for localization, GRβ was higher in the nucleus in the UMUC-3 with insulin, but not with Dex. There was no change in GRβ with insulin or Dex in the T24 cells. The GRα expression was significantly decreased ($p<0.001$) by insulin in the T24 cells, but no effect was observed in the UMUC-3 (FIGS. 3B & 3D). Dex treatment increased GRα protein in both cell lines, as well as translocation from the cytoplasm (control) to the nucleus (Dex). These results indicate a pro-growth pathway that involves the induction of GRβ and inhibition of GRα for proliferation or migration.

GRα Controlled Gene Transcription in Human Bladder Cancer Cells

Figure 4:
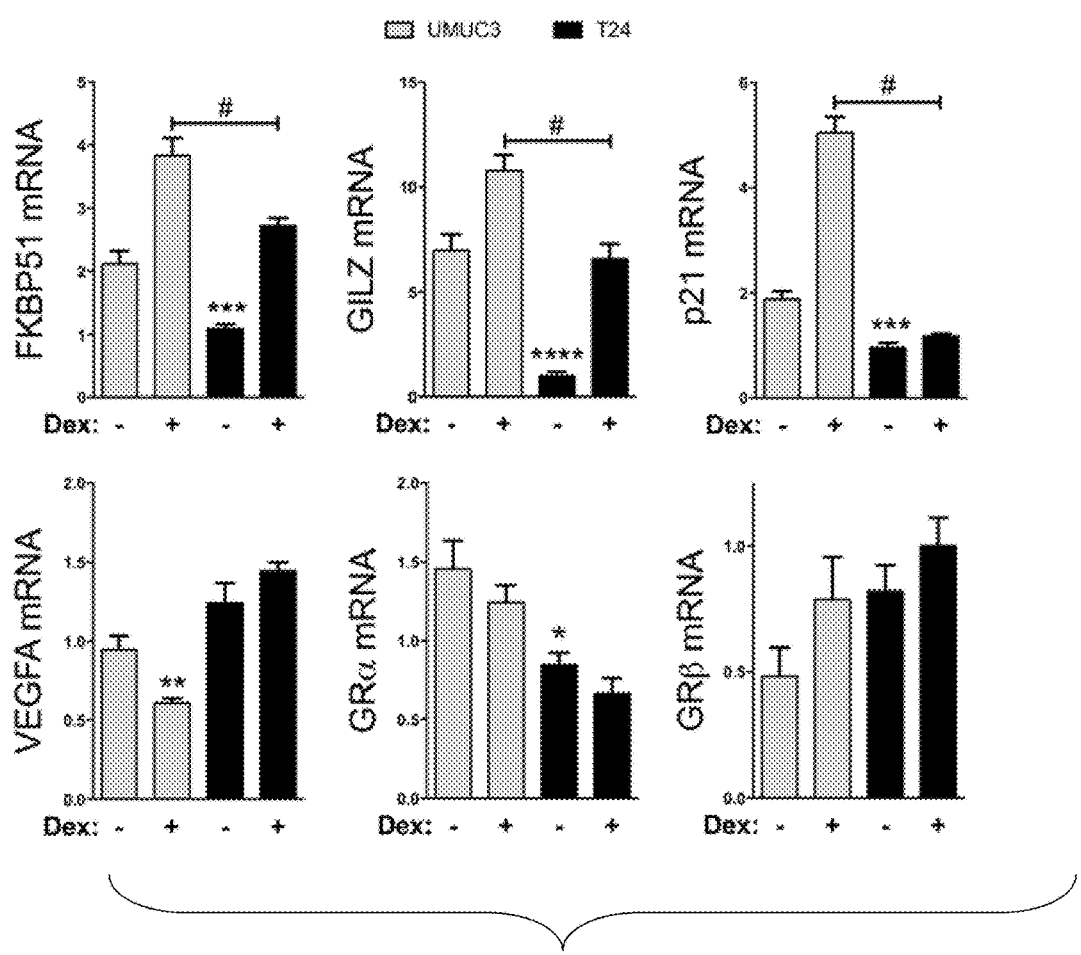
FIG. 4: GRα controlled gene expression in T24 and UMUC-3 human bladder cancer cells. GRα controlled gene response was measured by Real-Time PCR for FKBP51, GILZ, p21, VEGFA, GRα, and GRβ. Cells were seeded in media containing 10% dialyzed FBS for 24 hours before treatment. Cells were then treated with 100 nM dexamethasone or vehicle for 2 hours before mRNA was harvested. *, $p<0.05$; , $p<0.01$; *, $p<0.001$; ****, $p<0.0001$ (versus UMUC3 control); #, $p<0.05$ (versus UMUC3 Dex) (±S.E.; n=3).

The role of the GR isoforms in human bladder cancer is unknown, especially the gene regulator activity of GRα. To determine the GRα-induced gene activity in human bladder cancer cells, the T24 and UMUC-3 cells were treated with Dex for 2 hours. To test genes that are directly regulated by GRα, mRNA expression of known controlled genes FK506 binding protein 51 (FKBP51), glucocorticoid-induced leucine zipper (GILZ), and p21 (FIG. 4) was measured. The UMUC3 cell line was more responsive to the Dex treatment on FKBP51, GILZ, and p21 mRNA expression, likely due to the lower expression of GRβ leading to less GRα inhibition. The VEGFA expression was significantly ($p<0.01$) decreased by Dex treatment in the UMUC-3 cells, but not in the T24 cells. The GRα expression was significantly (p<0.05) lower in the T24 cells, but Dex treatment did not change the mRNA expression in UMUC-3 or T24 cells. The GRβ mRNA expression did not change with Dex treatments. However, it should be noted that the levels of GRβ and GRα mRNA are different than in FIG. 1B, which is due to the use of hormone-free serum for the glucocorticoid treatment.

GRβ Expression is Controlled by miRNAs

Figure 5:
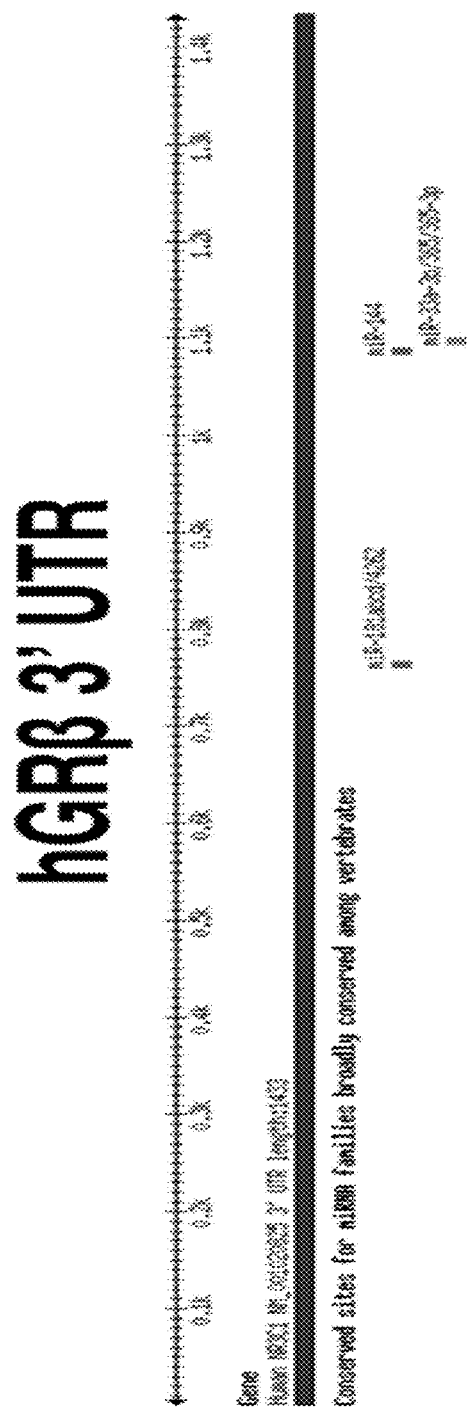
FIG. 5: In-silico analysis of potential miRNA binding sites of the 3'UTR of human GRβ, using human TargetScan (version 6.2) software.
Figure 6A:
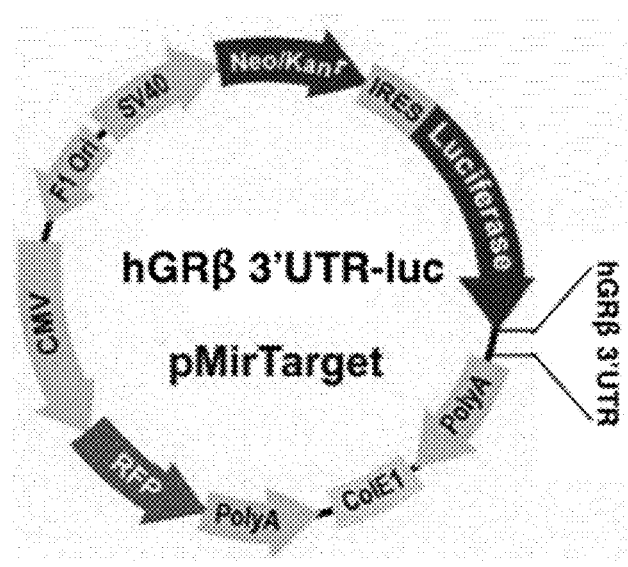
FIGS. 6A-6F: The human 3'UTR of GRβ is regulated by miR144. The pMirTarget vector containing the 3'UTR of human GRβ was cloned into a luciferase reporter gene (3'UTR GRβ-Luc) FIG. 6A). The T24 and UMUC-3 bladder cancer cells were transfected with the 3'UTR GRβ-Luc expression construct with mutation in the miRNA binding site for miR181, miR144, or miR33a and was measured by a luciferase assay, and normalized to renilla (FIG. 6B). *, $p<0.001$; **, $p<0.0001$ (versus WT) (±S.E.; n=6). The miRNA expression in the UMUC3 and T24 cells was measured using Real-Time PCR (FIG. 6C). *, $p<0.05$; **, $p<0.01$ (versus UMUC3) (±S.E.; n=3). Total RNA was harvested at the time of wounding and 3 hours after from the T24 cells in media containing 10% dialyzed FBS to determine the expression during migration assay for miRNA expression (FIG. 6D). *, $p<0.05$ (versus T0) (±S.E.; n=3), and for mRNA expression of GRβ and GRα expression (FIG. 6E). ***, $p<0.001$ (versus T0) (±S.E.; n=3). A plasmid containing the human miR144 in the pCMV-MIR vector was transfected in the T24 cells to show how miR144 overexpression affected the expression of GRβ and GRα as measured by Real-Time PCR (FIG. 6F). *, $p<0.05$ (versus T24 Vector) (±S.E.; n=3).
Figure 6B:
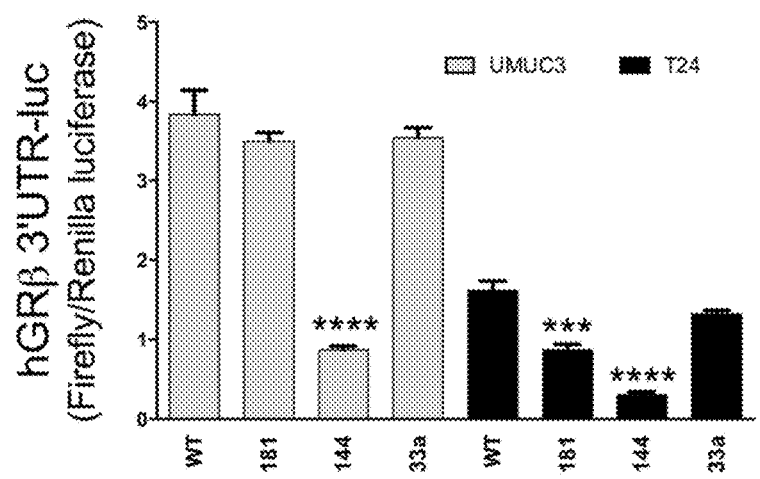
Figure 6C:
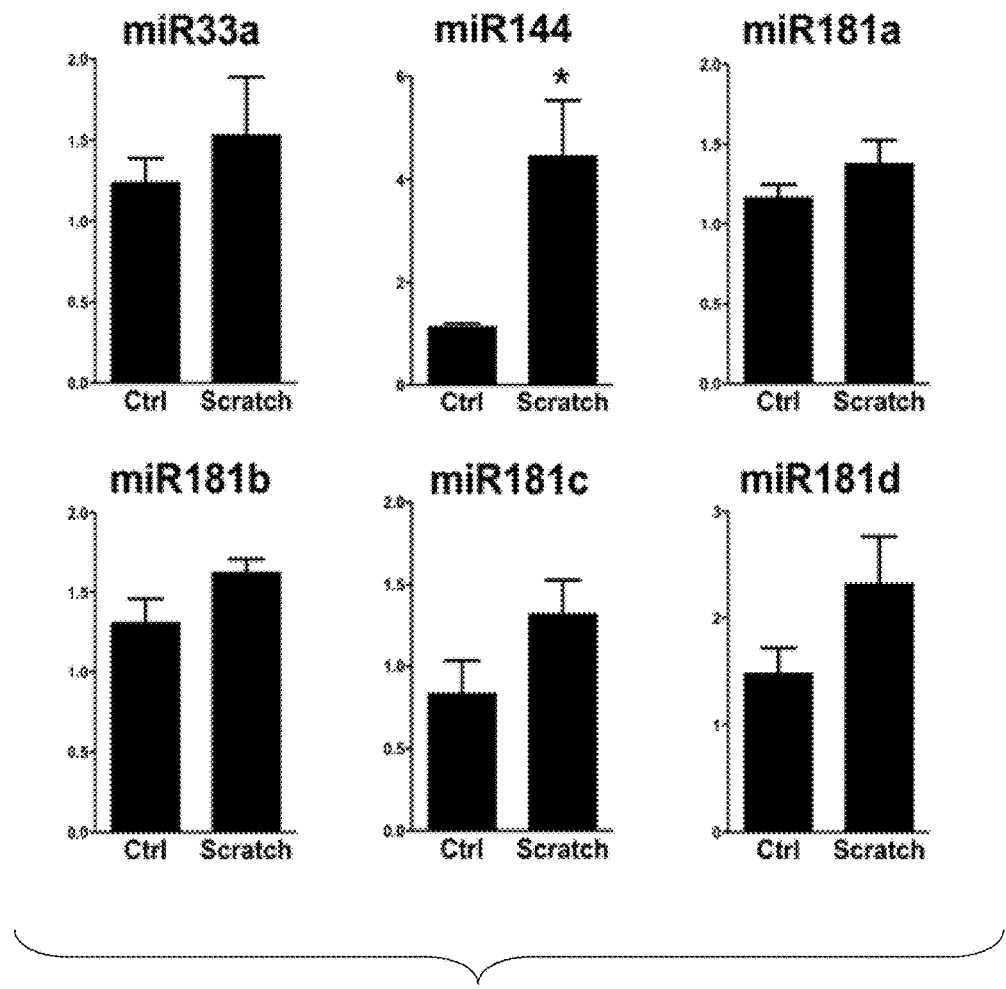
Figure 6D:
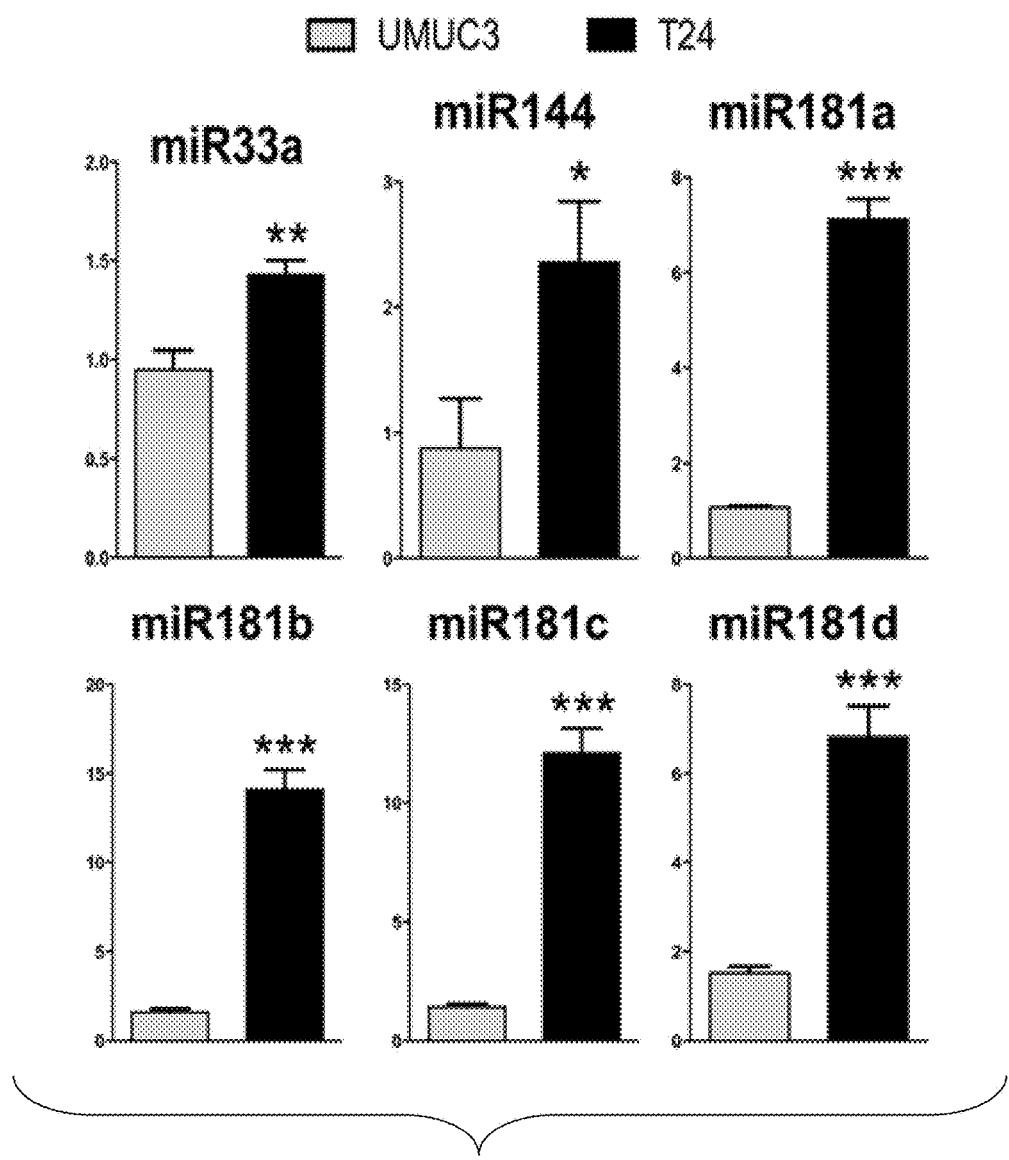
Figure 6E:
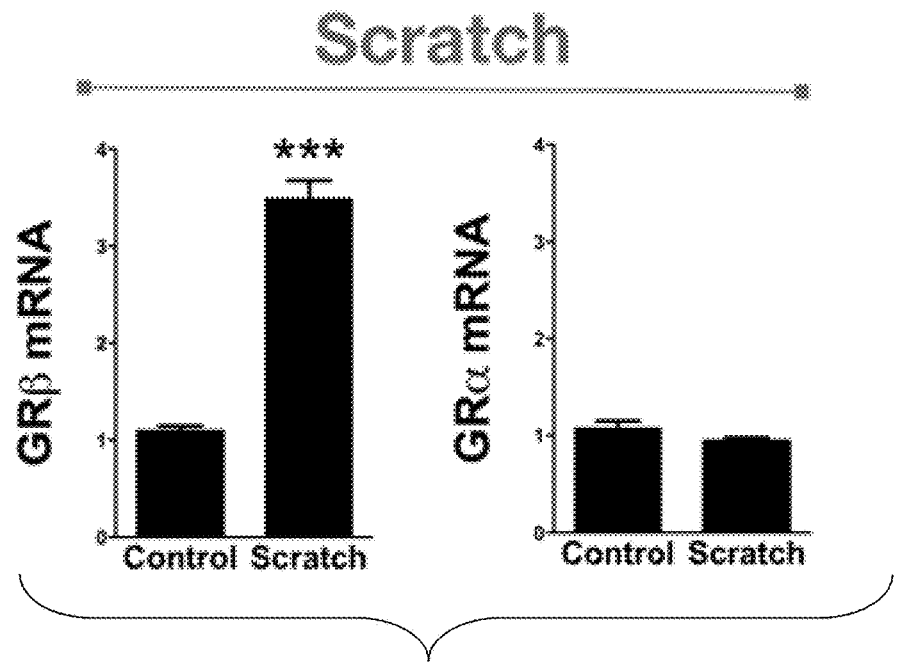
Figure 6F:
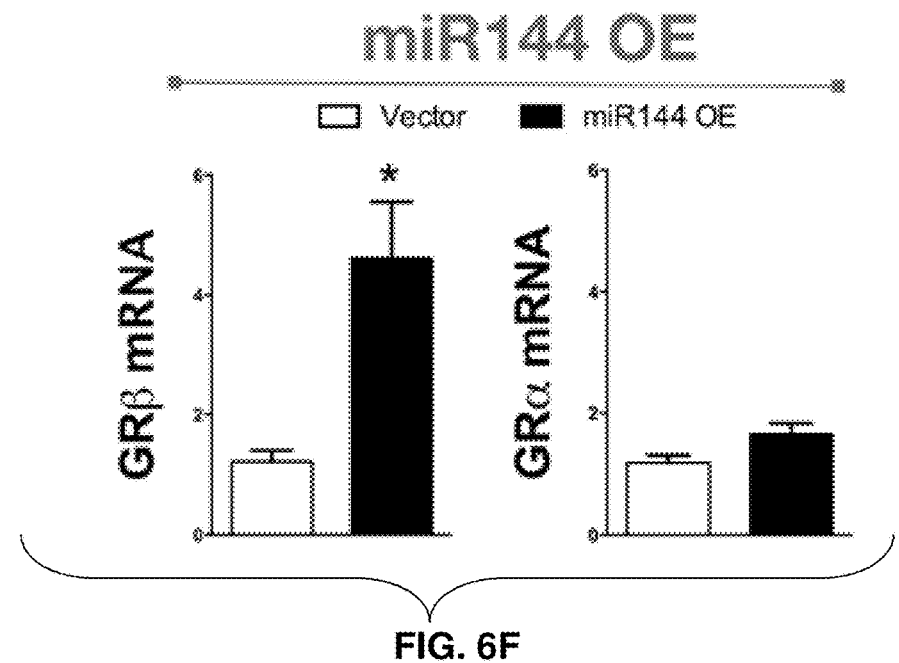

To assay miRNA control of GRβ expression, the in-silico prediction software Targetscan (version 6.2) was used to find miRNAs that may bind to the 3'-UTR of human GRβ (FIG. 5). Three miRNAs were predicted to bind the 3'UTR of human GRβ: miR-33a, miR-181-a/b/c/d, and miR-144. To determine which of the predicted miRNAs may regulate human GRβ expression, the pMirTarget vector was used with the 3' UTR of human GRβ (pMirTarget 3' UTR hGRβ) inserted after the luciferase reporter gene, which is under the control of the IRES promoter (FIG. 6A). Next, the predicted binding sites were mutated to all adenines (FIG. 7) to determine the potential of the miRNA on human GRβ expression. The UMUC-3 and T24 cells were transfected with the pMirTarget 3' UTR hGRβ mutants, and the luciferase activity was measured (FIG. 6B). Mutational analysis of the miR-144 binding site resulted in a decrease of 77% (UMUC-3) and 81% (T24) in the reporter expression, indicating that miR-144 enhances human GRβ expression. Mutation of the miR-181 site also decreased of luciferase in pMirTarget 3' UTR hGRβ, but this was not observed in the UMUC-3. Total RNA was extracted from the UMUC-3 and T24 cells to measure the miRNA expression of miR-33a, miR-144, miR-181a, miR-181b, miR-181c, and miR-181d (FIG. 6C). miR-181a, miR-181c, and miR-181d were increased in the T24 cells. Next, a scratch (wounding) assay was performed to determine if miR-33a, miR-144, miR-181a, miR-181b, miR-181c, or miR-181d changed during a scratch assay and if this affected the human GRβ or GRα expression. The scratch (wounding) assay of the T24 cell line showed that miR-144 (4 fold) and GRβ (3.2 fold) were both increased (FIGS. 5D & 5E). The miR-33a, miR-181a, miR-181b, miR-181c, and miR-181d were unchanged during the scratch (wounding) assay. GRα mRNA expression was also unchanged with the scratch (wounding) assay. To show that miR144 specifically regulates human GRβ, a plasmid containing the precursor of human miR-144 was overexpressed in pCMV-MIR or empty vector. The miR144-containing pCMV-MIR vector resulted in a 184-fold increase in miR-144 expression compared to the empty vector (p=0.002). The overexpression of miR-144 resulted in a significant (p<0.05) increase in human GRβ expression (3.8 fold), while not changing GRα (FIG. 5F).

Dexamethasone Control of Migration and miRNA Expression

Figure 8B:
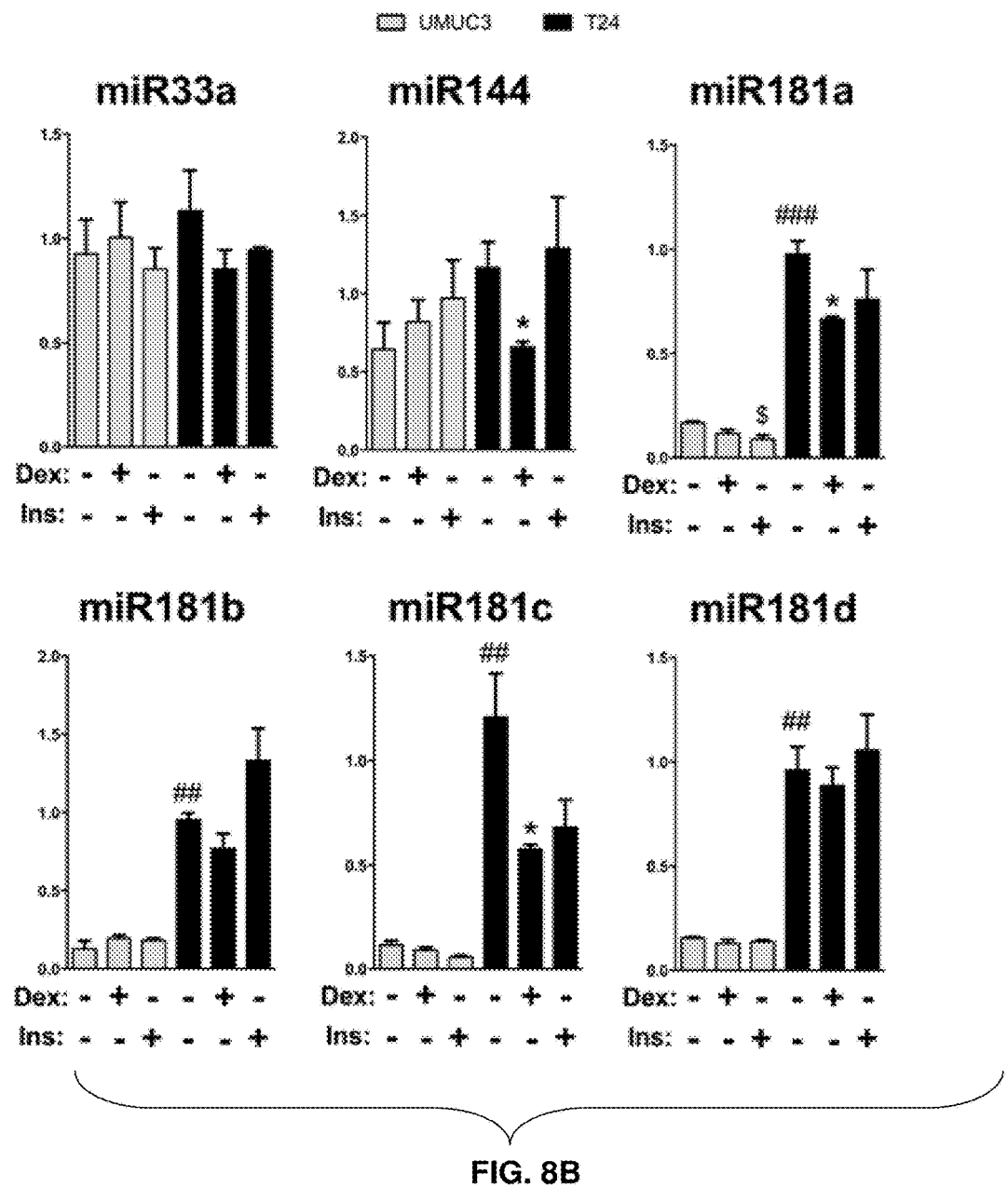

The effect of Dex on migration and regulation of miRNA expression was investigated. Dex treatment was performed 30 minutes before a scratch assay (wounding) of the T24 bladder cancer cells. The Dex treatment significantly (ANOVA: p<0.001) decreased migration, while there was no affect in the UMUC-3 cells (FIG. 8A). Dex treatment decreased expression of miR144, miR-181a, and miR-181c in the T24 cells, but not in the UMUC-3 cells (FIG. 8B). Insulin did not significantly change expression of miR-33a, miR-144, miR-181a, miR-181b, miR-181c, or miR-181d in the T24 cells. However, insulin did suppress miR-181a expression in the UMUC-3 cells.

Drug Targeting the miR144 Enhancement of GRβ

Figure 9A:
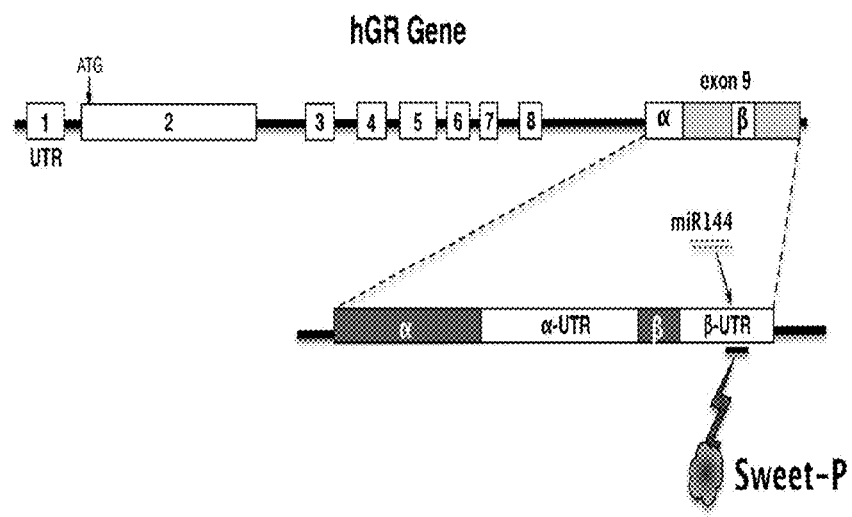
FIGS. 9A-9G: Blocking the miR144 binding site in the 3'UTR of human GRβ by Sweet-P inhibits expression and cell migration. A peptide nucleic acid (PNA) conjugated to a cell penetrating peptide (CPP) (Sweet-P) was designed to bind to the miR144 binding site in the 3'UTR of human GRβ mRNA (FIG. 9A). GRβ expression in T24 cells was measured at increasing doses of Sweet-P (0, 0.1, 1.0, 10, 50, and 100 nM) for 48 hours after and human GRβ mRNA was measured by Real-time PCR (FIG. 9B). ANOVA p<0.01; Dunnett's comparisons *, p<0.05; , p<0.01 (versus 0 nM) (±S.E.; n=6). The 3'UTR GRβ-Luc was used to determine the dose dependence of Sweet-P (0, 0.1, 1.0, and 10 nM) by luciferase (FIG. 9C). *, p<0.001 (versus 0 nM) (±S.E.; n=4).
Figure 9B:
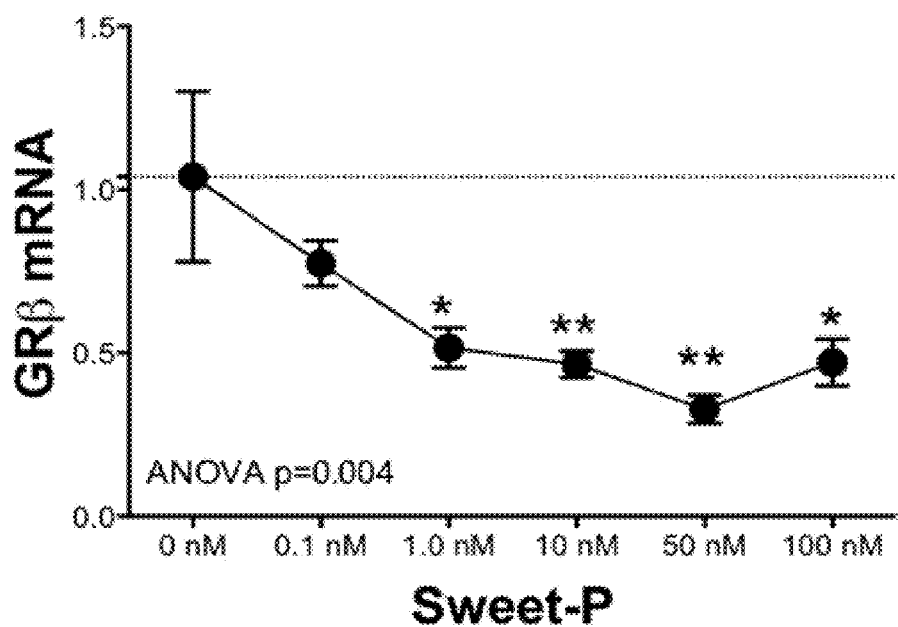
Figure 9C:
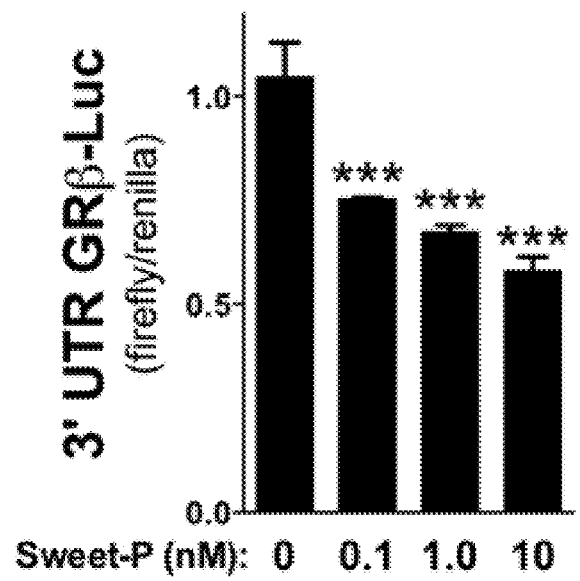
Figure 9D:
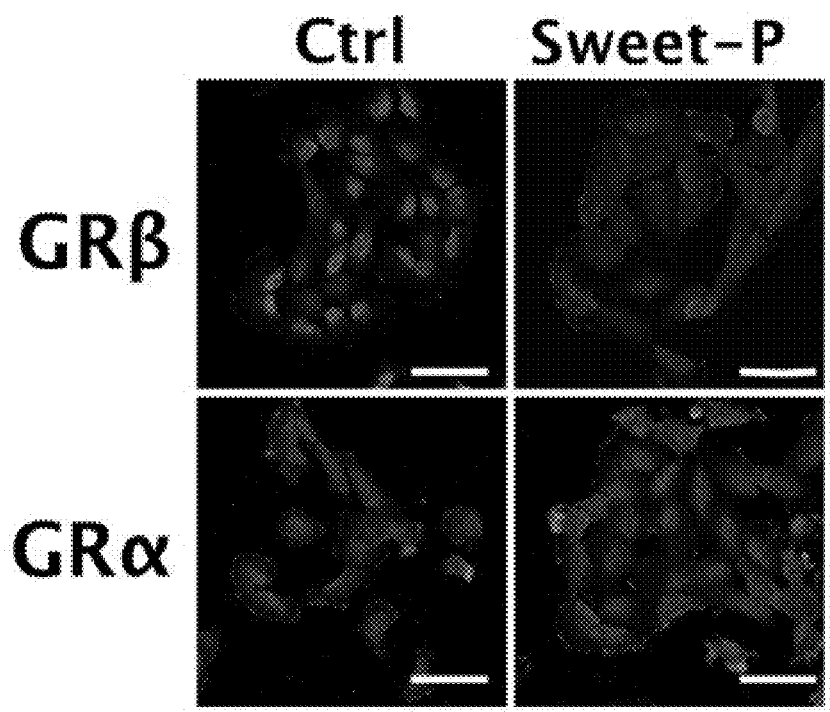
Figure 9E:
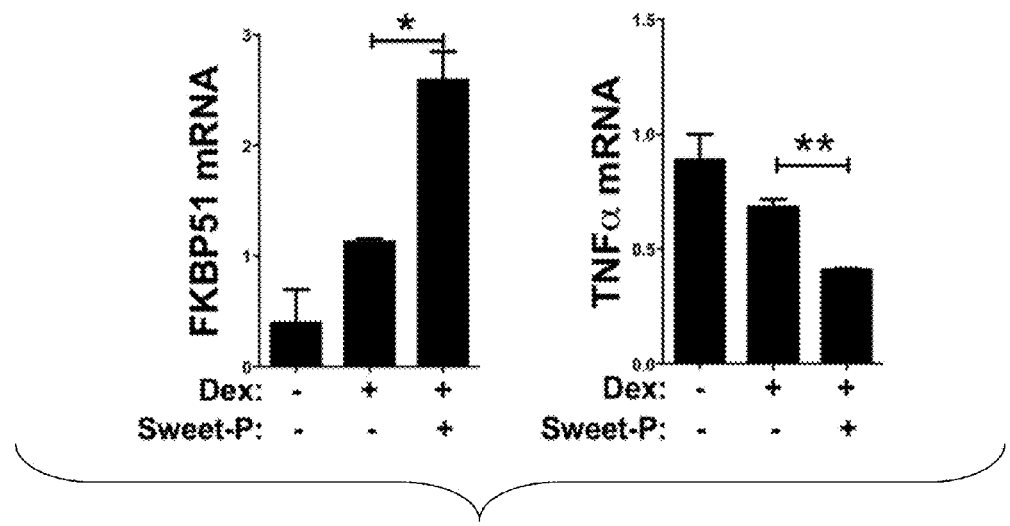
Figure 9F:
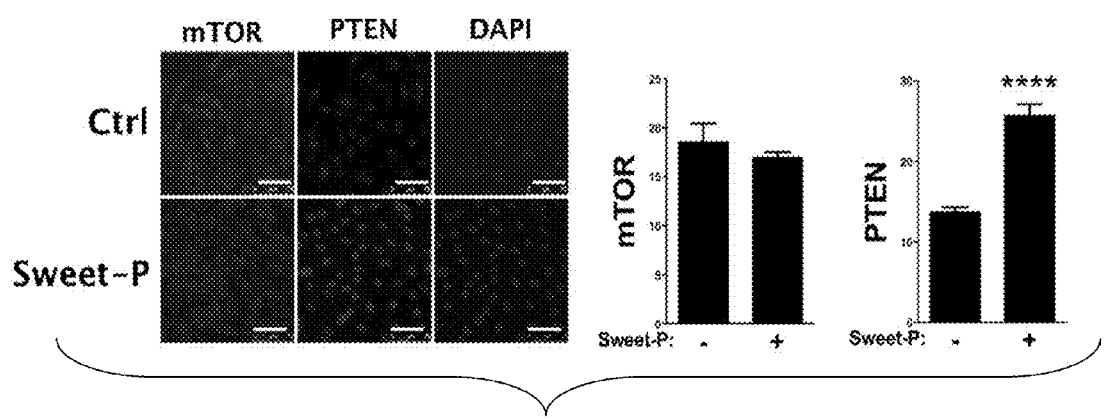
Figure 9G:
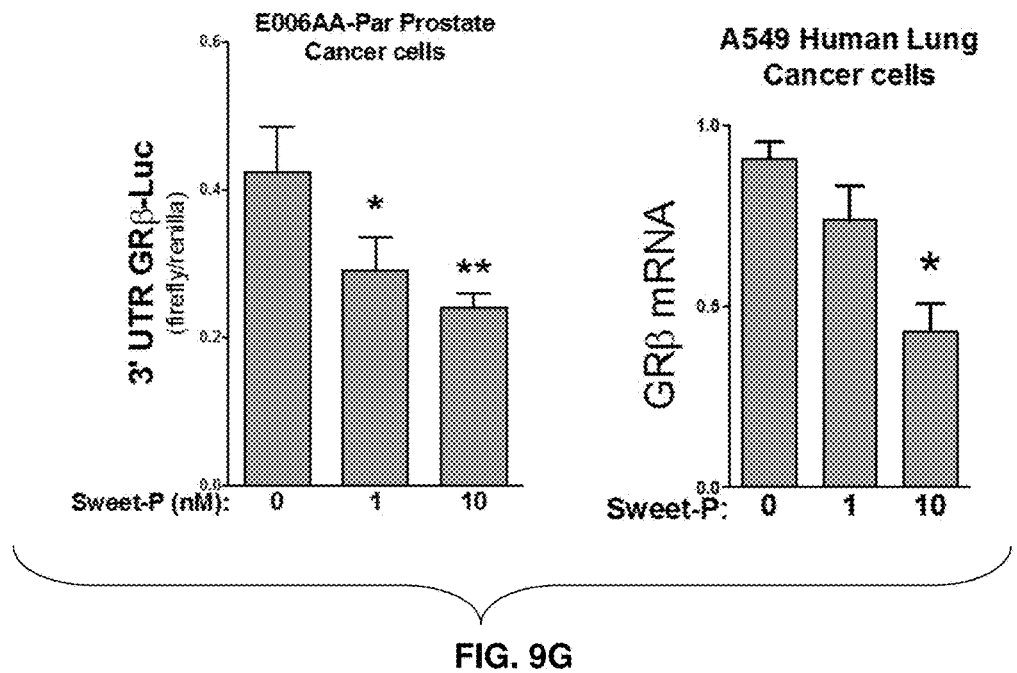

To inhibit the binding of miR-144 to the 3'UTR of GRβ, Sweet-P, a peptide nucleic acid (PNA) conjugated with a cell-penetrating peptide (CPP) targeting the site, was developed (FIG. 9A). A dose dependence response curve indicated that Sweet-P significantly (p<0.05) decreased GRβ mRNA expression in the T24 human bladder cancer at 1.0 nM, 10 nM, 50 nM, and 100 nM (FIG. 9B). To confirm the endogenous gene finding, the T24 bladder cancer cells were transfected with the pMirTarget 3' UTR hGRβ construct and treated with Sweet-P for 48 hours (FIG. 9C). The luciferase expression of the pMirTarget 3' UTR hGRβ construct was significantly (p<0.001) reduced at 0.1 nM, 1.0 nM, and 10 nM. Sweet-P (10 nM) reduced GRβ protein expression, but had no effect on GRα (FIG. 9D). Furthermore, Sweet-P significantly increased GRα activity with dexamethasone treatment by enhancing expression of FKBP51 (p<0.05) and decreasing a known GRα regulated gene, tumor necrosis factor α (TNFα) (FIG. 9E). To show that Sweet-P specifically targets the miR-144-binding site in the 3'UTR of hGRβ, protein expression of two known miR-144 targets that have been shown to be suppressed, PTEN and the mammalian target of rapamycin (mTOR), was measured by immunohistochemistry. The results show that mTOR expression was unaffected by Sweet-P (10 nM), and PTEN expression was significantly (p<0.0001) increased with treatment. To determine if Sweet-P could inhibit migration, the T24 bladder cancer cells were treated with 10 nM Sweet-P during a scratch (wounding) assay. The results show that Sweet-P significantly (ANOVA: p<0.001) inhibited migration of the T24 bladder cancer cells during migration (FIG. 9D).

Lung and Prostate Cancer Cells

Figure 10:
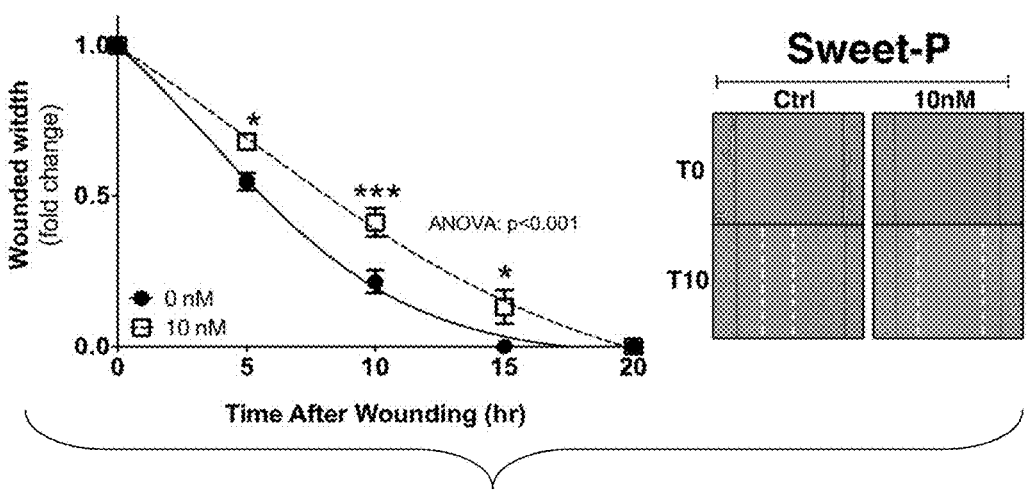
FIG. 10: Sweet-P blocks GRβ expression in lung and prostate cancer cells.

FIG. 10 shows that Sweet-P similarly blocks GRβ expression in A549 lung cancer cells and E006AA-Par prostate cancer cells.

Discussion

This is the first showing that GRβ is enhanced during the migration of human bladder cancer cells. Suppression of GRβ by lentiviral shRNA decreased the migration of T24 cells. GRβ increases the migration of astrocytes and brain cancer cells (glioblastoma). GRβ is elevated in cancers and inflammatory diseases, which leads to increased growth. GCs inhibit migration and proliferation of cancer cells in medulloblastoma, osteosarcomas, A549 human lung cancer cells, as well as other lung cancer cells: squamous cell carcinoma lines (EPLC-32M1 and NCI-H157), large-cell carcinoma cell line (LCLC-97TM1), and a cell line from mesothelioma (MSTO-211H). Without wishing to be bound by theory, it is believed that increasing GRβ provides a state of GC resistance that reduces their ability to inhibit growth and migration. Bombesin induces resistance to GCs by induction of GRβ in human prostate cancer cells. In these Examples, it is shown that the T24 human bladder cancer cells had a reduced response to GCs compared to the UMUC-3, which is believed to be due to elevated GRβ. The migratory potential of T24 cells, but not the UMUC3 cells, was inhibited by dexamethasone. Dexamethasone inhibits the invasion of bladder cancer cells, including the UMUC-3. Here it is shown that dexamethasone treatment inhibited miR-144, which is a positive regulator of GRβ and is increased during migration. Without wishing to be bound by theory, it is believed that the inhibition of miR-144 is a mechanism through which migration was reduced by dexamethasone in the T24 cells.

As shown by the mutation in the 3'UTR of human GRβ reporter, and plasmid overexpression, miR-144 is a positive regulator of human GRβ expression and not GRα. miR-144 downregulates the mammalian target of rapamycin (mTOR), a regulator of cellular growth and metabolism, and the loss of miR-144 leads to the progression of colorectal cancer.

Further, miR-144 downregulates PTEN expression, a tumor suppressor gene that regulates many cellular functions including cell proliferation, which is also suppressed by GRβ. miR-144 also inhibits bladder cancer proliferation by targeting the enhancer zeste homolog 2 (EZH2), a downstream regulator of the Wnt/β-catenin pathway that mediates growth. However, the effects of miR-144 on migration had not been previously investigated. There are a plethora of targets for miRNAs, and the specific blockade of miR-144 binding to the 3'UTR of GRβ by Sweet-P resulted in decreased GRβ mRNA expression and 3'UTR GRβ-luc reporter assay. The effect of Sweet-P was specific for the 3'UTR of human GRβ, as mTOR and PTEN, which are known to be suppressed by miR-144, were not lower but PTEN was significantly higher. GRβ binds to the PTEN promoter to inhibit expression. Sweet-P did suppress GRβ protein expression and resulted in no change in GRα.

Moreover, the downregulation of GRβ by Sweet-P inhibited migration of bladder cancer cells, indicating that Sweet-P serves as a therapy for bladder cancer. The inhibitory effect of dexamethasone on the migration of the T24 cells supports the notion that GRα is a suppressor of bladder cancer, which is also shown by Sweet-P enhancing GRα activity and suppressing migration of the bladder cancer cells. Dexamethasone inhibition of VEGF-A also demonstrates that GCs inhibit bladder cancer, as VEGF-A levels have been found to be greater in higher grade urothelial tumors. Dexamethasone decreased miR144 and migration of the T24 cells, which indicates that suppression of miR144 levels also reduces GRβ expression. However, two-hour dexamethasone treatment in hormone-free serum did not affect GRβ mRNA, and 30-minute treatment did not change the protein. Glucocorticoids may alter GRβ expression with longer treatment. GRβ increases in mouse fibroblasts with dexamethasone treatment, but no change has been observed in mouse C2C12 myoblasts. During migration, dexamethasone suppression of miR-144 may have a larger impact on GRβ expression.

The effect of insulin on enhancing GRβ expression and inhibiting GRα indicates that it increases the risk of bladder cancer. However, insulin did not increase miR-144 expression with an acute two-hour treatment, which indicates that it enhances GRβ levels by a different mechanism. The effect of insulin on cancer cell migration rate has not been investigated, but the insulin-like growth factor receptor I (IGF-I) has been shown to promote invasion of bladder cancer cells through an Akt and mitogen activated protein kinase (MAPK) dependent mechanism. There has been no correlation found for bladder cancer in insulin-resistant type II diabetics, which indicates that insulin may not have a role. Without wishing to be bound by theory, it is believed that IGF-I may signal to GRβ to increase bladder cancer invasion, though the effect of IGF-I on GRβ expression has not been investigated. Without wishing to be bound by theory, it is believed that the increase of miR-144 during T24 migration and its enhancement of GRβ expression are mediated in a non-insulin dependent manner. Two drugs for the treatment of type II diabetes, rosiglitazone and pioglitazone, have been shown to induce bladder cancer, but their effect on miR-144 or GRβ expression is unknown. There is a 3:1 incidence in men compared to women for bladder cancer, which may be mediated by the androgen receptor (AR). Without wishing to be bound by theory, it is believed that there may be an interaction between AR and GRβ in prostate cancer. It has been shown that suppression of GRβ in LNCaP, RC165, and DU145 human prostate cancer cells inhibited growth. However, the signaling involvement of GRβ and AR in bladder cancer has not been investigated.

GRβ mediates bladder cancer migration and serves as a target for therapy. The 3'UTR of GRβ is enhanced by miR-144 during human bladder cancer migration. Blocking the interaction of miR144 with the 3' UTR of GRβ by Sweet-P slowed bladder cancer migration. The antagonism of human GRβ by Sweet-P, drug interaction, or gene targeting is useful as a treatment for bladder cancer.

Example 2

Figure 11A:
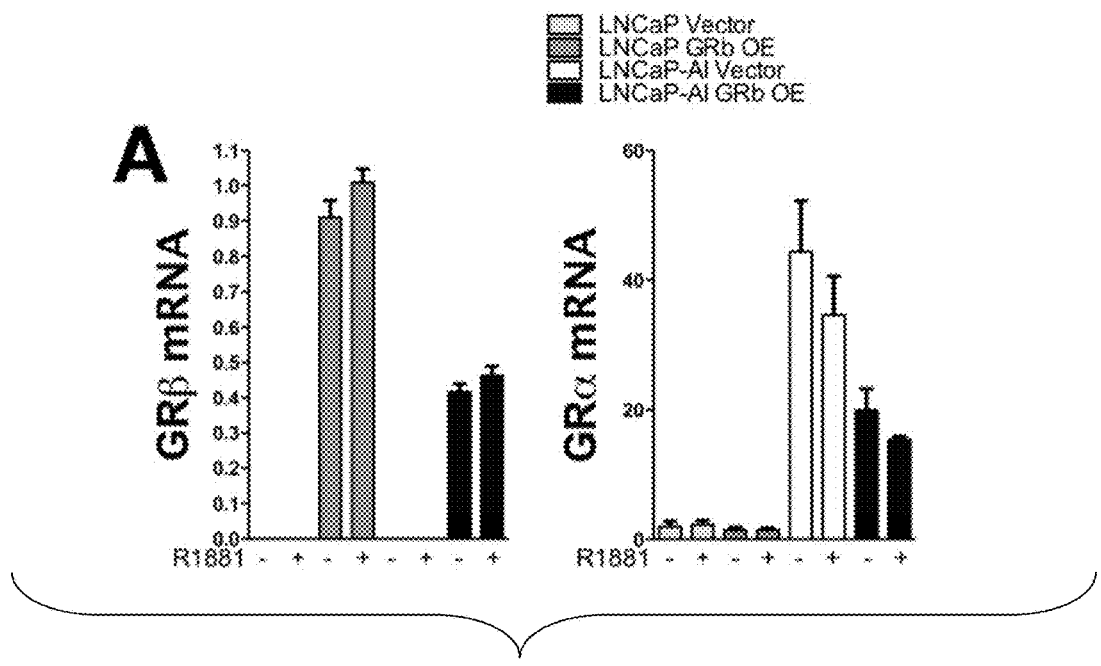
FIGS. 11A-11C: GRβ selectively regulates AR activity. LNCaP cells were stably infected with lentivirus containing GRβ cDNA or vector. Cells were plated in hormone-free dialyzed FBS for 24 hr and treated with R1881 androgen for 2 h. Real-time expression of (FIG. 11A) GRβ and GRα, (FIG. 11B) Nkx3.1, and (FIG. 11C) SGK. N=3; , P<0.01; *, P<0.001 vs ctrl. #, P<0.05; ##, P<0.01; ###, P<0.001 vs R1881 treated vector.
Figures 11B, 11C:
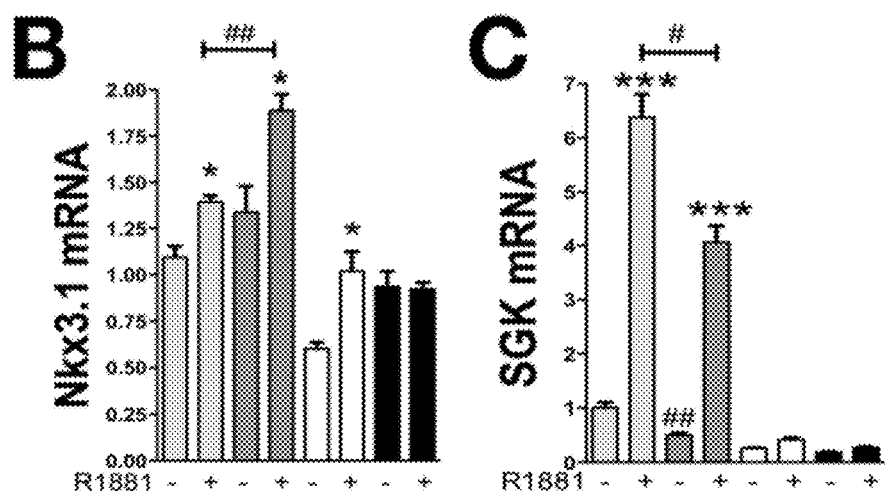

Overexpression of GRβ selectively regulated AR transcriptional activity (FIGS. 11A-11C). The overexpression of GRβ increased Nkx3.1 mRNA expression more than R1881 androgen treatment in vector controls. However, GRβ OE suppressed AR activity at the serum-induced glucocorticoid kinase (SGK) promoter. The LNCaP-AI cells did not respond to androgens, as these cells are androgen independent in proliferation assays. Overall, these data show that GRβ has specific actions on the transcriptional ability of AR. GRβ may interact with a particular set of genes with AR in the prostate to control growth. As discussed herein, the AF-1 region in AA men compared to CA has been shown to have fewer CAG repeats and this may enhance the ability of GRβ-AR to dimerize.

Determination Whether CAG Repeat Number Alters GRβ-AR to Dimerization.

GRβ selectively increases Akt1 expression over that of Akt2. Importantly, Akt1 was shown to be significantly higher in prostate cancer specimens of African Americans compared to European American men. Akt signaling increases the expression of AR and transactivation. Also, Akt blocks ligand binding and protects against expanded polyglutamine AR toxicity. Increased AR levels were associated with higher clinical stage and PSA levels, as well as an earlier relapse after radical prostatectomy. However, in the late stages of prostate cancer androgen ablation therapy is not effective. There has been a correlation between increased phosph-Akt and a higher Gleason score, which may result in androgen independence. This is now believed to be due to elevated GRβ expression, which increases phospho-Akt in serum free conditions, and exacerbated with insulin treatments. The GRβ/Akt1 growth axis is now believed to have an important function in the regulation of AR activity, and as described herein, is now believed to regulate specific gene activity based on CAG repeats in AR. This indicates a positive feedback between GCs/GRα and PTEN in the suppression of growth, which is attenuated by GRβ. Additionally, Akt 1 is a direct target of the PI3K induced growth pathway, and has also has a major role in cancer.

Figure 12A:
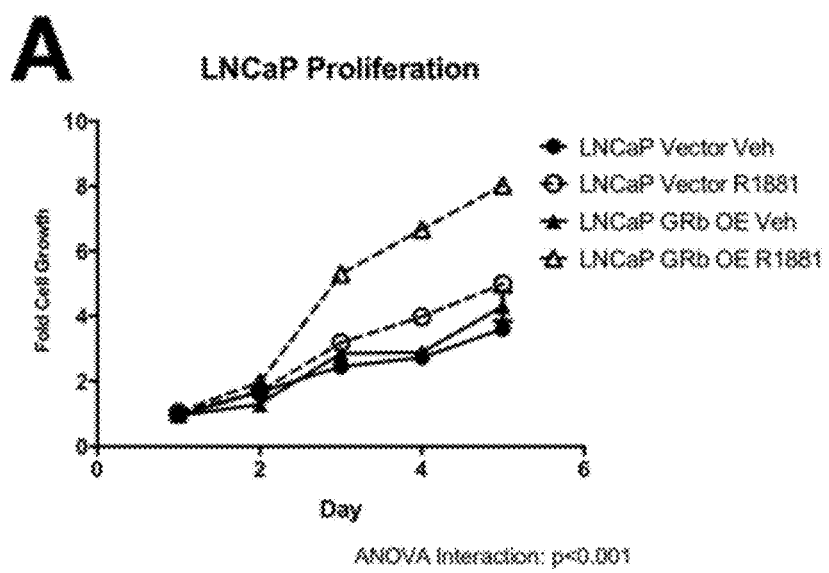
FIGS. 12A-12C: GRβ increases androgen induced growth in LNCaP cells. Overexpression of hGRβ cDNA in LNCaP cells via lentivirus increased androgen induced growth, but not in the androgen insenstivie LNCaP-AI. **, P<0.01 (LNCaP vector vs LNCaP GRβ OE). N=12.
Figure 12B:
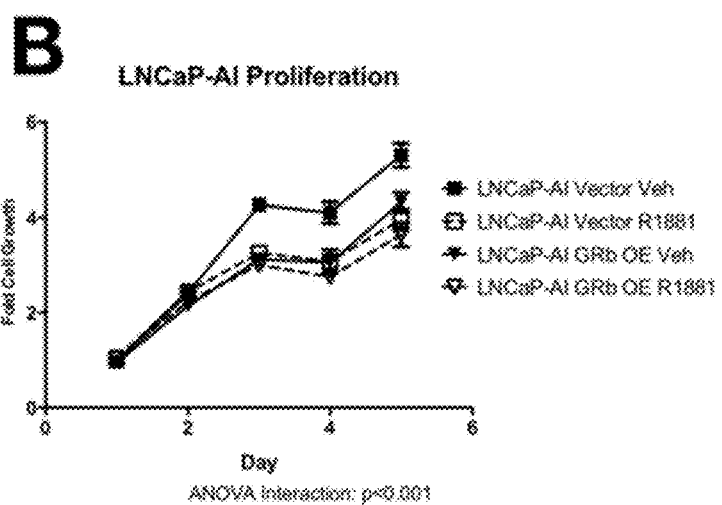
Figure 12C:
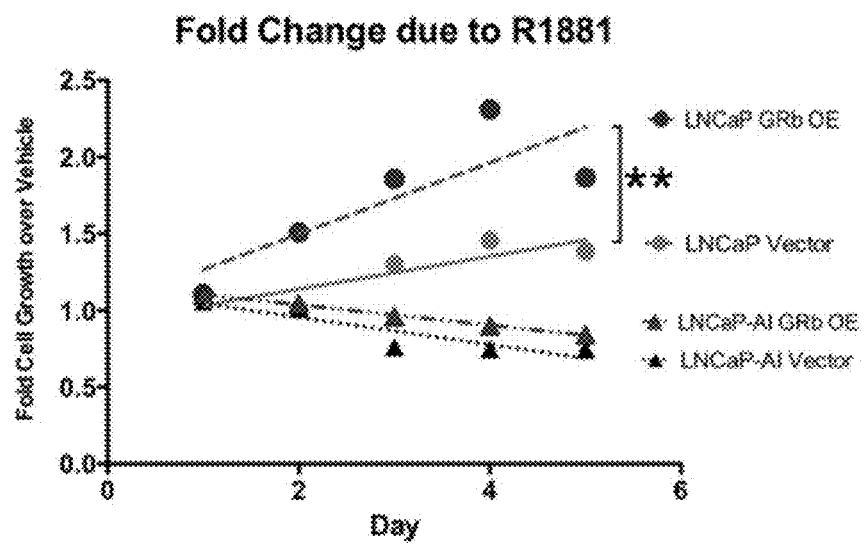

FIGS. 12A-12C show that increased GRβ levels resulted in the enhancement of androgen-induced growth. Interestingly, bombesin treatment attenuated GC-induced apoptosis in PC-3 human prostate cancer cells by increasing GRβ expression.

Role of GRβ in AR and GRα Signaling

Figures 13A, 13B:
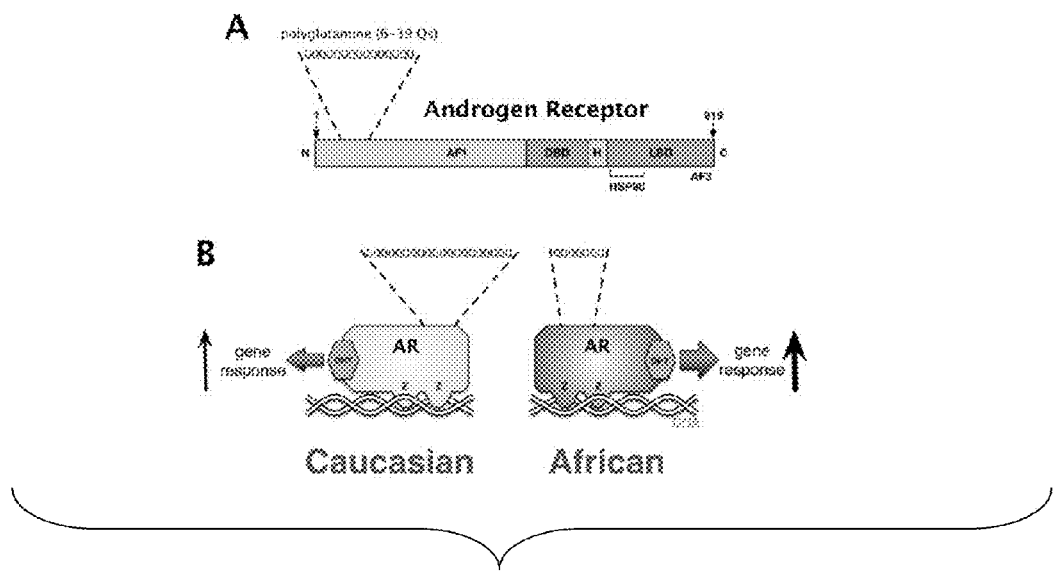
FIGS. 13A-13B: AR gene structure and comparison of Caucasian and African American AR signaling.

To determine differences in GRβ or GRα expression in prostate cancer cell lines from different ethnicities, prostate cancer cell lines that originated from African American descent, E006AA-Par and E006AA-hT were obtained, as well as from Caucasian lineage, LNCaP and LNCaP-AI. The E006AA-Par cell line is not tumorigenic in nude mice. However, the cell line is responsive to androgen-induced growth and expresses AR with 26 CAG repeats in exon1, but does not express PSA. AR is a member of the nuclear receptor family, and consists of three functional domains: an amino-terminal activation factor-1 (AF-1) domain, a central DNA-binding domain (DBD), and a carboxy-terminal ligand-binding domain (LBD) (FIG. 13A). Two polymorphic trinucleotide repeats (CAG and GGC) have been found in exon 1 of the AR gene. The CAG repeats encode for a polyglutamine chain located upstream of the AF-1 domain, and as a result causes an adverse effect on AR function. In particular, an inverse relationship exists between the number of CAG repeats and AR transcriptional activity. A shorter CAG repeat has higher AR activity (42) and is associated with an elevated risk of developing PC. AA men have significantly shorter CAG repeats in comparison to CA men (FIG. 13B), which may, in part, explain the AR variation between the two ethnic groups that potentially contribute to the disparity. The AR expression is much lower in the E006AA-hT cells compared to the E006AA-Par.

In comparison to the Caucasian derived LNCaP and LNCaP-AI cells, the expression of GRβ and GRα was much higher in the African American E006AA-Par and E006AA-hT cells (FIGS. 14A-14B).

GRβ was significantly (p<0.05) higher in the more tumorigenic and aggressive E006AA-hT cells, compared to the E006AA-Pa. However, the LNCaP cells have very low to no expression of GRβ and GRα. Suppression of GRβ by lentiviral shRNA in the African American prostate cancer cells (E006AA) caused a significant reduction in migration (FIG. 15).

Figure 16:
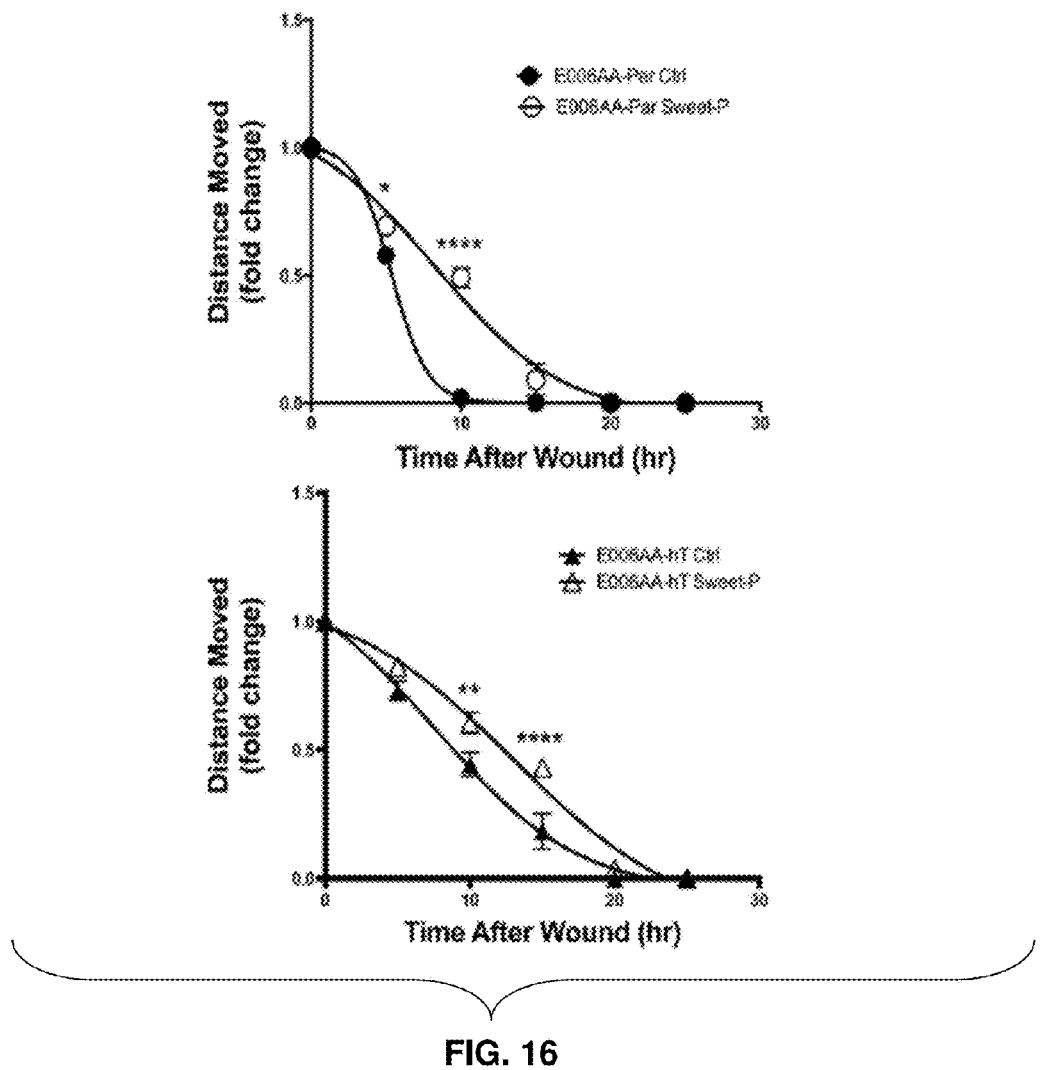
FIG. 16: Sweet-P suppression of human GRβ in E006AA-Par and E006AA-hT African American prostate cancer cells suppresses migration. *, P<0.05; , P<0.01; *, P<0.001; ****, P<0.0001; (scramble vs GRβ KD). N=12.

The anti-GRβ molecule Sweet-P, also significantly decreased migration in the E006AA cell lines (FIG. 16). The mechanism that underlies the roles of GRβ on androgen and glucocorticoid signaling can be determined in the African American prostate cancer cells, E006AA-Par and E006AA-hT, as well as the LNCaP and LNCaP-AI cell lines (including heterodimerization, DNA-binding and promoter occupancy properties.

Transcriptional activity of AR and GRα activity is measured at reporter and endogenous genes following GRβ over-expression or knockdown using the viral vectors developed in FIG. 15. Expression is by Western blotting, Real-time PCR, and immunohistochemistry (FIG. 17 & FIG. 18), which also determines the localization of the GRs in different cells.

GRβ and GRα expression is measured in the cells, as well as in an array of different human prostate cancer cells that are of known ethnicity, such as African-American cells (MDA PCa 2a, and MDA PCa 2b, and Caucasians cells (RWPE, VCaP, PC-3 and DU-145.

The GRβ and GRα expression levels of prostate cancer cells of unknown origin (CWR22, 22Ry1, LACP-4, and ALVA101) are also measured.

Determination Whether GRβ Regulate AR or GRα Differently in African American and Caucasian Prostate Cancer Cell Lines African American men are more susceptible to prostate cancer, and because AR is known to have differences in the amount of CAG repeats between the populations, the GRβ may affect the signaling differently by heterodimerization on promoters. GCs inhibit growth and induce apoptosis in prostate cancer cells, and there is now believed to be a relationship to the resistance to GCs, due to elevated GRβ in the prostate, and a higher incidence of prostate cancer in these patients.

Determination Whether GRβ Inhibits the Apoptotic Actions of GRα in the African American (E006AAPar and E006AA-hT) and Caucasian (LNCaP and LNCaP-AI) Prostate Cancer Cells.

The cells are treated with GCs (dexamethasone) and androgens (R1881) and subsequently measured for expression of GRβ, GRα, PTEN, phospho-Akt, and phospho-AR (serines 81 and 650) by Western blotting. The phosphorylation of GRβ and GRα at three serines known to regulate activity (S203, S211, and S226 are measured. AR activity is measured by treatment with the androgen R1881. GRα and AR activity is measured via Real-time PCR at known target genes: GILZ, FKBP51, PSA, and VEGFA. Lentiviral knockdown and overexpression of human GRβ are used to determine if this also affects GRα and AR activity. The growth inhibitory properties of GCs are measured in the African American and Caucasian prostate cancer cell lines by MTT proliferation assay. Growth and activity are compared to the ability of GRα to bind to hormone in each cell line (hormone binding assays are also performed. Higher total GR proteins and low binding indicate a GC-resistant state, which may be due to high GRβ proteins. Additionally, the effect on migration and invasion in the E006AA-Par, E006AA-hT, LNCaP, and LNCaP-AI cell lines with and without glucocorticoids and androgens are measured. Migration and invasion are assessed in vitro via simple scratch assays and/or laser scanning confocal imaging of 3D transwell migration assays to determine differences in GC and/or androgen treatment to determine the chemotactic and invasive capacity of the different cell lines GRβ mediates the activity of AR in a gene selective manner (FIGS. 9A-9C), indicated that GRβ has an important role in prostate cell homeostasis, growth, and/or cancer.

Determination of Any Differential Expression in GRβ or GRα Levels in Prostate Cancer Specimens From African Americans or Caucasians African American men are more predisposed to the development of prostate cancer over Caucasians (16-18, 60), and develop higher grade more aggressive tumors. There are known growth inhibitory roles of GCs in prostate cancer.

Figure 17:
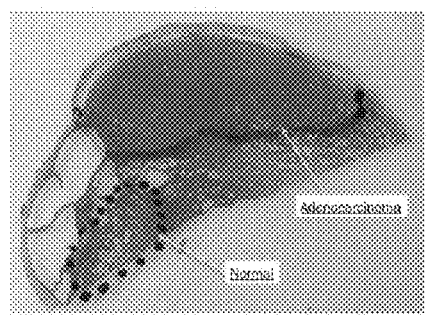
FIG. 17. Human prostate specimens identified as cancerous or normal.
Figure 18:
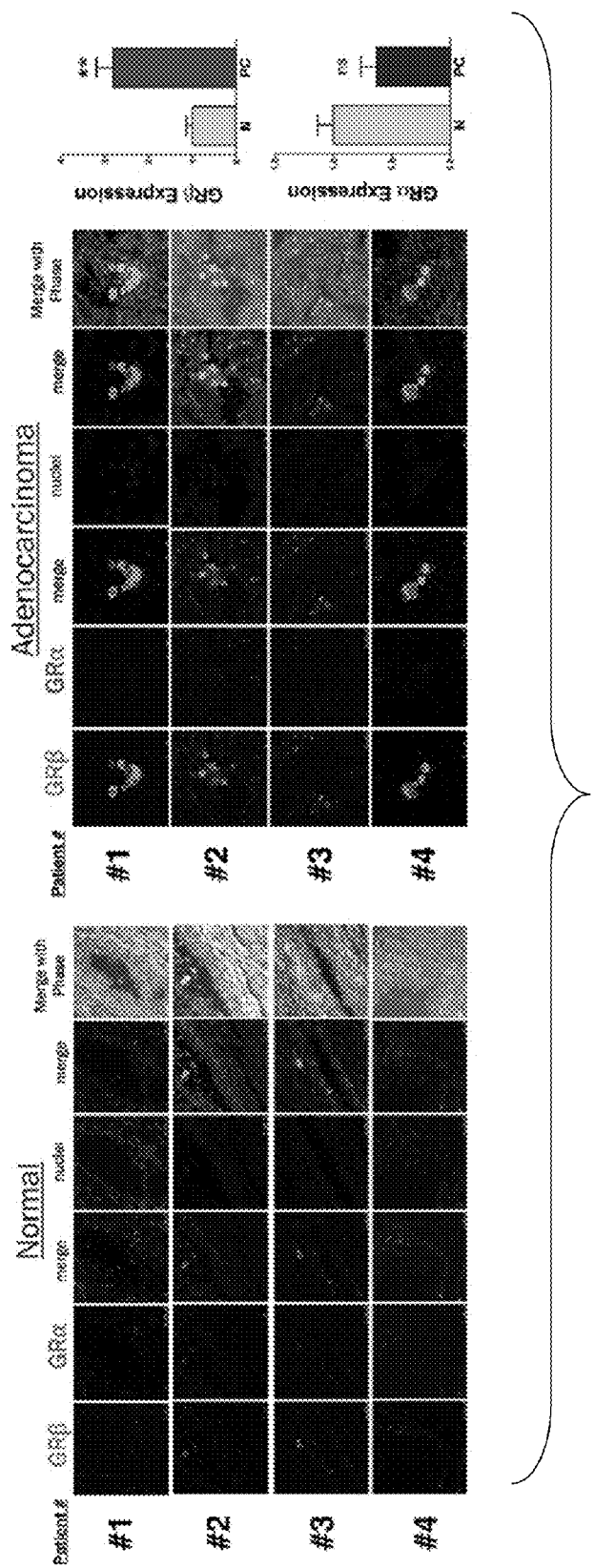
FIG. 18: GRβ & GRα staining in prostate samples from patients.

The data now show that GRβ can inhibit expression of the tumor suppressor gene, PTEN (FIGS. 11A-11C), and it also suppresses the activity of GRα resulting in the enhancement of growth, as well as androgen-induced growth (FIGS. 12A-12C). African American men may have a higher basal expression of GRβ that increases their incidence of the development of prostate cancer. To determine the role of GRβ and GRα in normal and malignant prostate epithelial cells of African American and Caucasian men, archived prostate specimens are used. To show whether GRβ or GRα expression levels in normal and prostatic cancer, whole prostates removed at the time of radical prostatectomy were examined. The prostate cancer patient specimens had been were declassified. Cancerous and normal regions were identified by H&E staining by the Pathologist (FIG. 17). To determine GRβ and GRα expression in normal and prostatic cancer, commercially available GRα and GRβ antibodies for costaining on the same tissue specimen were used. It is now shown that GRβ significantly (p<0.05) increased in adenocarcinomas of the four patients tested (FIG. 18).

Certain embodiments of the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composition comprising a peptide nucleic acid (PNA) consisting of the sequence TGCCATACACAGTAT [SEQ ID NO:1].

2. The composition of claim 1, wherein the PNA is attached to a solubility enhancing molecule.

3. The composition of claim 2, wherein the solubility enhancing molecule comprises an O-linker.

4. The composition of claim 1, wherein the PNA is conjugated to a cell-penetrating peptide.

5. The composition of claim 4, wherein the cell-penetrating peptide comprises a modified tat protein.

6. The composition of claim 5, wherein the modified tat protein consists of the amino acid sequence VQRKRQKLMP [SEQ ID NO:2].

7. The composition of claim 1, wherein the PNA is attached to an 0-linker and to a modified tat protein consisting of the amino acid sequence VQRKRQKLMP [SEQ ID NO:2].

8. A peptide nucleic acid (PNA) consisting of the sequence TGCCATACACAGTAT [SEQ ID NO:1].

9. A pharmaceutical composition comprising:
an effective amount of the composition of claim 1; and
a pharmaceutically acceptable carrier, diluent, or adjuvant.

10. A method of modulating GRβ expression in cells, the method comprising:
administering to cells an effective amount of an agent which binds to the glucocorticoid receptor gene and is capable of blocking miR144 binding to GRβ, and modulating GRβ expression in the cells; wherein the agent comprises a PNA consisting of the sequence TGCCATACACAGTAT [SEQ ID NO:1].

11. The method of claim 10, wherein the cells are cancer cells.

12. The method of claim 10, wherein the cells are in a human subject.

13. A method of treating a GRβ-related disease, the method comprising:
administering an effective amount of an agent comprising the composition of claim 1 to a subject in need thereof, wherein the effective amount of the agent binds to the glucorticoid receptor gene and blocks miR144 binding to GRβ in the subject, and treating a GRβ-related disease in the subject.

14. The method of claim 13, wherein the agent is conjugated to a modified tat protein.

15. The method of claim 13, wherein the GRβ-related disease is selected from the group consisting of: bladder cancer, prostate cancer, lung cancer, liver cancer, fatty liver disease, glioblastoma, leukemia, lupus, and asthma.

16. A method of hindering migration of a GRβ-related disease, the method comprising administering an effective amount of a composition of claim 1 to a subject in need thereof and hindering migration of a GRβ-related disease.

17. The method of claim 16, wherein the GRβ-related disease is selected from the group consisting of bladder cancer, prostate cancer, lung cancer, liver cancer, fatty liver disease, glioblastoma, and leukemia.

18. The method of claim 16, wherein the subject is a human subject.

19. A method for regulating GRβ expression in cells, the method comprising administering an effective amount of a composition of claim 1 to cells and regulating expression of GRβ in the cells.

20. The method of claim 19, wherein GRβ is suppressed in the cells.

21. The method of claim 19, wherein the cells are cancer cells or liver cells.

22. The method of claim 21, wherein the cancer cells are selected from the group consisting of bladder cancer, prostate cancer, lung cancer, liver cancer, glioblastoma, and leukemia.

23. The method of claim 19, wherein the cells are in a human subject.

24. A kit for preparing a pharmaceutical composition, the kit comprising:
a first container housing a peptide nucleic acid (PNA) consisting of the sequence TGCCATACACAGTAT [SEQ ID NO:1]; and
a second container housing an O-linker or a modified tat protein consisting of the amino acid sequence VQRKRQKLMP [SEQ ID NO:2].

* * * * *

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgccatacac agtat                                                     15

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Gln Arg Lys Arg Gln Lys Leu Met Pro
1               5                   10

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccagaaagca catctcacac attaatctg                                      29

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Gln Gln Gln
1

<210> SEQ ID NO 5
<211> LENGTH: 1436
<212> TYPE: DNA
<213> ORGANISM: Homo sapiens

<400> SEQUENCE: 5
tgattttcat cccaacaatc ttggcgctca aaaaatagaa ctcaatgaga aaagaagat      60 tatgtgcact tcgttgtcaa taataagtca actgatgctc atcgacaact ataggaggct    120
tttcattaaa tgggaaaaga agctgtgccc ttttaggata cgtgggggaa agaaagtca    180 tcttaattat gtttaattgt ggatttaagt gctatatggt ggtgctgttt gaaagcagat    240
ttatttccta tgtatgtgtt atctggccat cccaacccaa actgttgaag tttgtagtaa    300
```

-continued

```
cttcagtgag agttggttac tcacaacaaa tcctgaaaag tattttttagt gtttgtaggt    360 attctgtggg atactataca agcagaactg aggcacttag gacataacac ttttggggta    420
tatatatcca aatgcctaaa actatgggag gaaaccttgg ccaccccaaa aggaaaacta    480
acatgatttg tgtctatgaa gtgctggata attagcatgg gatgagctct gggcatgcca    540
tgaaggaaag ccacgctccc ttcagaattc agaggcaggg agcaattcca gtttcaccta    600
agtctcataa ttttagttcc cttttaaaaa ccctgaaaac tacatcacca tggaatgaaa    660
aatattgtta tacaatacat tgatctgtca aacttccaga accatggtag ccttcagtga    720
gatttccatc ttggctggtc actccctgac tgtagctgta ggtgaatgtg ttttttgtgtg    780 tgtgtgtctg gttttagtgt cagaagggaa ataaaagtgt aaggaggaca ctttaaaccc    840
tttgggtgga gtttcgtaat ttcccagact attttcaagc aacctggtcc acccaggatt    900
agtgaccagg ttttcaggaa aggatttgct tctctctaga aaatgtctga aaggatttta    960 tttctgatg aaaggctgta tgaaaatacc ctcctcaaat aacttgctta actacatata    1020
gattcaagtg tgtcaatatt ctattttgta tattaaatgc tatataatgg ggacaaatct    1080
atattatact gtgtatggca ttattaagaa gcttttttcat tatttttttat cacagtaatt    1140 ttaaaatgtg taaaaattaa aaccagtgac tcctgtttaa aaataaaagt tgtagttttt    1200
tattcatgct gaataataat ctgtagttaa aaaaaaagtg tcttttttacc tacgcagtga    1260 aatgtcagac tgtaaaacct tgtgtggaaa tgtttaactt ttatttttttc atttaaattt    1320 gctgttctgg tattaccaaa ccacacatttt gtaccgaatt ggcagtaaat gttagccatt    1380
tacagcaatg ccaaatatgg agaaacatca taataaaaaa atctgctttt tcatta        1436
```

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Gln Gln Gln Gln Gln Gln Gln Gln Gln Gln Gln Gln Gln
1               5                   10                  15

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Gln Gln Gln Gln Gln Gln Gln Gln Gln Gln Gln Gln Gln
1               5                   10                  15

Gln Gln Gln Gln
            20

<210> SEQ ID NO 8
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 8

Gln Gln Gln Gln Gln Gln Gln
1               5
```